(12) United States Patent
Yoon et al.

(10) Patent No.: US 12,274,721 B2
(45) Date of Patent: Apr. 15, 2025

(54) COMPOSITIONS AND METHODS FOR INHIBITING THE PROLIFERATION OF ENTEROTOXIGENIC BACTEROIDES FRAGILIS

(71) Applicant: iNtRON Biotechnology, Inc., Gyeonggi-do (KR)

(72) Inventors: Seong Jun Yoon, Seoul (KR); Jee Soo Son, Seoul (KR); In Hwang Kim, Gyeonggi-do (KR); Hyoung Rok Paik, Incheon (KR); Eun Kyoung Oh, Gyeonggi-do (KR); Soo Youn Jun, Seoul (KR); Sang Hyeon Kang, Seoul (KR)

(73) Assignee: iNtRON Biotechnology, Inc., Gyeonggi-do (KR)

( * ) Notice: Subject to any disclaimer, the term of this patent is extended or adjusted under 35 U.S.C. 154(b) by 0 days.

(21) Appl. No.: 18/498,391

(22) Filed: Oct. 31, 2023

(65) Prior Publication Data

US 2024/0050499 A1    Feb. 15, 2024

Related U.S. Application Data

(63) Continuation of application No. 17/227,286, filed on Apr. 10, 2021, now abandoned.

(51) Int. Cl.
*A61K 35/76* (2015.01)
*A61P 31/04* (2006.01)

(52) U.S. Cl.
CPC .............. *A61K 35/76* (2013.01); *A61P 31/04* (2018.01)

(58) Field of Classification Search
None
See application file for complete search history.

(56) References Cited

FOREIGN PATENT DOCUMENTS

WO    WO-2014070225 A1 *  5/2014 ........... A61K 35/742

OTHER PUBLICATIONS

Tariq, M.A. et al. 2020. Genome characterization of a novel wastewater Bacteroides fragilis bacteriophage (vB_BfrS_23) and its host GB124. Frontiers in Microbiology 11: 1-12 plus Supplementary Data; specif. pp. 1, 4, 10 (Year: 2020).*
NCBI Blast sequence search. Seq ID No. 1. Datasheet [online]. Retrieved on Aug. 5, 2024. Downloaded from the internet: <https://www.ncbi.nlm.nih.gov/nucelotide/MT630433.1&report=genbank$log$=nucltop&blast_rank=13&RID=B1UXNDVH016> pp. 1-3 (Year: 2024).*
NCBI ORFinder. Open Reading Frame Finder. Seq ID No. 1. Retrieved on Dec. 27, 2022. Downloaded from the internet: <https://www.ncbi.nlm.nih.gov/orffinder/> pp. 1-2.
Tariq, M.A. et al. 2020. Genome characterization of a novel wastewater Bacteroides fragilis bacteriophage (vB_BfrS_23) and its host GB124. Frontiers in Microbiology 11: 1-12; specif. pp. 1, 3.
NCBI Blast. Nucleotide sequence search. Seq ID No. 1. Retrieved on Dec. 27, 2022. Downloaded from the internet: <https://www.ncbi.nlm.nih.gov/nucleotide/MT630433.1?report=genbank&log$=nucltop&blast_rank=4&RID=UPP327G2013> pp. 1-3.
Zaczek-Moczydlowska, M.A. et al. 2020. Genomic characterization, formulation and efficacy in planta of a Siphoviridae and Podoviridae protection cocktail against the bacterial pathogens *Pectobacterium* spp. Viruses 12(150): 1-16; specif. p. 2.

\* cited by examiner

*Primary Examiner* — Adam Weidner
*Assistant Examiner* — Sharon M. Papciak
(74) *Attorney, Agent, or Firm* — SIMI Law Group, PC

(57) ABSTRACT

A composition for preventing or treating an infection or disease caused by enterotoxigenic *Bacteroides fragilis* includes a Siphoviridae bacteriophage (Bac-FRP-4) having an ability to lyse the enterotoxigenic *Bacteroides fragilis* cells and a pharmaceutically acceptable carrier. A method for preventing or treating an infection or disease caused by enterotoxigenic *Bacteroides fragilis* includes administering to a subject a Siphoviridae bacteriophage and lysing the enterotoxigenic *Bacteroides fragilis* cells by the Siphoviridae bacteriophage.

5 Claims, 4 Drawing Sheets

Specification includes a Sequence Listing.

SEQUENCE LISTING

```
Sequence total quantity: 1
SEQ ID NO: 1              moltype = DNA  length = 46960
FEATURE                   Location/Qualifiers
misc_feature              1..46960
                          note = Siphoviridae bacteriophage
source                    1..46960
                          mol_type = other DNA
                          organism = unidentified
SEQUENCE: 1
gctaataagg atatgttcgg tttgacctat gaccctcaaa aaaggtatta tgtgtttata   60
gatcattctg ttctatcatc tacaattcct aatgacacaa gaagtatctt tttgcggatc  120
gtatacactg atggcacaag cgaggacatg tcggtattta atgacagcat aggaaacaat  180
ttcatcctta catcaaaggc tattagatac atattgggtt cttatggtac ttctgtctcg  240
acttacttgc gtattggaat attttgaaaca aactttcctg tttcatggag tcccgcaccg  300
gaagatcaat tataccagtc tgttaagtac acagatactc aaattttggc agttgatggt  360
aagatagaac tatctgtaac aacggaatta aataaacgtg tcattggtgg cgctaatttg  420
atattaaaat cgggtacatg tgtttccggt gttgacaggg aagaacgttt tgatatgtcc  480
caatatttta gagatttgag agggaagaaa gttactattc cttttgatta tgaatatagt  540
aatttggaat taggtcgtga aaatcgaata ggtcttgaag agccagtatt gaaagacgga  600
acttcccaat attattgggt gggtactttt aaacatttca attcttcgtc accgaaatct  660
gaaaaaggac gatttgttaa tactattacg gtacccgatg atattgtaac ctctcagaat  720
aaagggatat acttaattat tcaagtaggg aatggtacaa acatgaaagt ttgcaatcct  780
cagattgaaa tcggagatac tgcaactggg tggagtcctg caccagaaga tggaataata  840
gaatctaagg aatatactaa tagtcaaatt agtgtagtcg aaggtaagat aacatccacc  900
gttgaaaaga taaataccgt tgatggacgt gttaccggac ttgcttcacg cgtcgaacag  960
accgaaaaaa gtatcacgtc tgttgttggt gatattggtg ttattaatag taccaccaat 1020
aggcatatat caaagcgaat agatttaaga ggatgggaca ataataagtt tttcccgttg 1080
gttataagta ttccggttta ccacaaaaca agggttgaaa taagtaggcc tcttaatgcg 1140
ggatacggaa aaccttcata cggtactcac gatggcggtt tttctatgaa cttaacgttt 1200
gagatgtccg gttcggggtg gggttcgttg ccagcagtaa ccaatatctt tgactatact 1260
aaagcatgga cttctgcggg tgcaaagata gttgttgatt tgggacaaat aactgaaacg 1320
tctacgtgta gaatgggtat tagggcggt tctatgtatg acgtaaccgt atatgatact 1380
attgacccaa acgtaatcaa cgtttatcaa accgattatc acggttcgta taatacatcg 1440
ttccccgttc gcaccgatgg aactgaaccc gtccgcacat acggatacta taccgaaata 1500
aagcagacgc aggaaagcat agctttaact gcgaacaaag tggacgatca aggtaggcga 1560
ttaagtgcgg ctgagttaac tctaagttca gaccacgcaa aattaagcgt agtagaacaa 1620
gcggcaaatt ccgccaattc cttagcaggc acagccaata acaaagccga agccgcagac 1680
ggtcgtgtca ccgccaccca aaacggctta gtcgaaaccg gaatcaacat cacgtcccgc 1740
aaaatcgtgc taaagtctga taacgtcctt ttccaaaaca acgcaggaca gcagacagcc 1800
gctatcaatg cgaacgggaa acttactgca aatgcaatcg aggttgggaga agttgttgcc 1860
ggaggttttg cggctcagag aattactacc gggaacttga ctgtgacgga tggggctgtt 1920
atcggtggta tgactatcaa agggggagtg ctgaccggga agaacatcaa tatacaggat 1980
ggtgcaaaga tcggtaactt caccattgta tcgggtatat tttccgccca aaatacgccc 2040
gcaggcatac aaatgactct atcgaataat gccgctactt ttgacagtag cggagtacgt 2100
gtagaacata attcggttgg ttatcgcttg actactacgg gtaaccgaag agtgttctta 2160
acaggttcaa atttttgggt tcagtgtaag gacgttgatt ttatgggtgc tcaaacatgg 2220
aaagcccegg gtgtttttta cgcatgtacg attttggcaa acggagcaat cggtaaaaca 2280
tggggggaacc ctgactttca tataacaaga gtaactaaga actcaacagg gagatatact 2340
gttaatacta ccggttccaa tggggactac tttgttatga ttacagcgta tcatcctaca 2400
agttggttaa gtacaacagt agaaccatac tcagaaggac agtttgcgta caaagtattc 2460
gatgtaaata ctggcatgac tgacagcgga gttattattt atttttgtgg catggttagg 2520
tagtttagtg ttttaattaa cggtaagttg gtttttatcct tcttaccgtt taccttttgta 2580
```

```
ccaaacatta atcaattaat ataaaattat ggaaaagaaa agtttagatt ttgatttaaa    2640
gtcagtagtt tacacgaaag aaacaaaagt gatggactac catttcgaga cggaaaacgg    2700
caagtacgta ggtcaattaa caacggtatc gacagagccg gacaagtaca acattaccca    2760
ctgtacggct gatgtgtcag agaaacaaat ggtagaaatg ccgggaacta ccggtagtcc    2820
aattctgcaa gaacaatacg ttccggtcgg atcgcttgcc atccgtgacg gtcgctttga    2880
ggcaaaccag tttcctctat ctactaaaac atccgtctat gtgaacgact ttcaaaattt    2940
catctttgcg ttaaccgcac ctaaaacagt agaataatga atgttacaca agaacagtta    3000
aggttaatgc ttgtatcggc aattagtccg atacttgcgt ttctcacccc tacgagcggt    3060
tttataaccg cccttgtgtt catgtttggc tttaacatta tttgcggcat gcgtgccgat    3120
ggggttaatt tgtcggtaaa tggtgttcgt aggttcacta tgctgaaatt catctcagcc    3180
gtgcaggaac ttattttgta catccttgtg ataaccgtta tcttttcgtc tgtggctaag    3240
atgggggatc acgacgcagc cgttctatcg gcaaagacga ttacatacgt ctttatgtac    3300
gtatatctgt cgaacggttt taagaacctt tgtatcagct acccggataa caaatctttc    3360
cggttgatat accacattgt ccggtttgag tttaagaggc tgatggggaa gaacgcatca    3420
aagatagtcg aggaacacga agaaaagatt gagattgaaa ctaagtaatt aacatgggag    3480
gtttaacgcc tcccttaac ctttatcaga atgaagtatt ttacattaaa agagctaaca    3540
cgctcagcaa cggcagaggc aaaaggtatt gataacacgc ctacgccgga agttgaaaag    3600
aacttaaagt tattggtaga taatgtactt gataaattac gtgagattta cggcaagccg    3660
atcacggtta attcgggtta tcggtgtccg gagttaaaca aagccgtcgg aggatctaaa    3720
acatccgatc acgttaaagg ttttgcggct gatattaccg gaggcagcaa ggaagagaac    3780
gaacgccttt tcaatatcat taagcacaat ttccatttca aacaattaat aaacgagaaa    3840
gatttttcat gggtgcatgt ctcctacgat ccctctaata tcaaaaacca aatactaaaa    3900
ctatgaaacg acaattattt gcgttttag cgacttttgt gctttgcctt ggtattgtgt    3960
cgctattact gataaacgct gatttacgga agaaaaaagc tattgcagaa agaaatgtta    4020
gcgtcctcac aactcagaac gttgcgtacc ggacgaaaag cggtcaaagt gccatgaaag    4080
tagaggaatt gaatctaact ttaaggcagt accggaacac tatacagggg aaggataaca    4140
ccataaaaga gctaaagcag tctatcaagg acttgaaaag tcacacaagc gttcaaatat    4200
caactgaggc gcattttagc acggctgtac gggatagtat tgttattctt gatagtttgg    4260
ttatcgcacac aatgaaatgc gtaaatattc gctctaaatg gattgactta ccggctgta    4320
tagatagcaa cggcacgttt gccggaacaa ccgttacccg tgatgcttg gaaatactaa    4380
atatagagca tagaaagagg tttttgtggt ttagactaaa gaaggtgaag tatagagagt    4440
ttattgtaac gagcaaaaac ccctacgctg agataacagg ttttaacgta actacgataa    4500
taaagtgata attccatgtt aaaacagtta atgcacgtta aagtattgc tactgagaaa    4560
tatatccgta tatttgcagc gtagaagtta ttactaacgt cattaacagc ggttattgat    4620
tttcacagaa tcatgttttt ggaagatttg tatcacattt tatcttaaac tgtcggtatg    4680
agaatataga cagttttaa ttagaacatt ttcactaact atatatattg ggttttgtca    4740
taattacatt tttcccctc cgcttgtgaa agtagagggg tttttatta ccttatccga    4800
acacgtctaa aaagttaaat tagtgttaaa tatcaaactt atgctttgat attaaaata    4860
tctcctaac ttcgcgacat caaaaggaaa cgaattacta acaataaaac ttagagttat    4920
ggaagaaaag gaatttattt attgcttgac cggagagatt aacgtattag gcactgtcaa    4980
ggctaagaca ataaaaagtg ctatgaaact tgtagcggct attcagagag gtgctatatt    5040
gaatgatccg gaaggaaat caatcttttg gagcgtttca cgtgctgatc tcccgttaa    5100
acttggtcgt attgtgtata caatatgcta ttccgatggt tctgtccgtt cacatgtgtg    5160
ctaacaataa aaaattagaa ttatgatacg atcgtttaat aagtcgggtt caacatctat    5220
gctgacagat aaggaaaaag cgtttaaccg atactgccta actaacaagg aagtttcata    5280
caacttaatg cgtatagaaa tggcagttgt tcaaatgtcg tattacggca accgttcatc    5340
ggacgttacg ttaacaaccg atagttctga ggtcttggat gcaatttata cagtcctaac    5400
aaatgaaggg tttaaatact ctttcaattt acctaataaa gtattaacca taagtatttt    5460
ttaatttaaa atttaatcaa aatgaaagaa gaagtaaat tgttcagagc gttaattatt    5520
gtttttgtgt cgcttgtatt caccttcgta gtaacttcat gcagtgatga tagcgacaat    5580
gtgatcaaa cagagtattc tattgatgta ccggagtggc aaactgttta tgtgaatggt    5640
gaggttacaa cgtctatatc accatatgtt tgggaacatg tggacttatc agataaatgt    5700
gttagggtat tctccgcagg acatgttagt tatcacaagg taacgagggt gtcacgtgat    5760
gatttaggct ttaccgttta ttcaatagaa ggtagcaata acgaaaggtt tgcatacaat    5820
aaaaataaag gtatattgca atattggtgc acaagaaacg agttgttgtt    5880
tatcgtgaat taaagtaagt ttcattttac cctcacccgg tggcggttaa ccgggttatt    5940
aagtatgaaa gtaaatgttc tattagaaga gaaaaagatt ccatgtttcg aagctaaata    6000
cggttagatg tatataacga taaggacaaa aaatatacta tcgagttcga tataatggga    6060
aatttagtag ttagtagtcc aaaaggtacg ttattagtaa aacccgaatg taacaacaaa    6120
atatcaatta gaattgaatg atatgaaaga gataaacgaa actcaattac agctatcgac    6180
tgagggaaaa agacttcccg atatgataaa gcaggcgaac gatattcacg aacttgttaa    6240
gcagaaactt tctgagtata actcaataga gtataccgat gataatataa aggtggcaaa    6300
agccgataga gctactttaa acaaggcgaa aaagggactt aacgcacagcc gtatagaact    6360
tgaaaaggct tggatgaaac cgttcaacga actaaaggat gttgttaacg aaacttgtaa    6420
gctgatcggt gaggcttctt cgcgcataga tagcaagata aaggaaacgg aggaaaagga    6480
gaagcaaaag aaactggatc aaataaggga gtatttcgag gaacacaatg aaaatcttat    6540
cttgtttgat tttgctttcc gtccggagtg gcttaataag actaaagcac tttcagttgt    6600
gaaaatggag atagacgaat tgttcaaaac agtagacgat gatcttaaca gactgaaaga    6660
gcattttgcg ggagaggcgt tttatattcc ggttatcgaa aaatatacgt ctacactcga    6720
ctacaacaaa tcattcgact atggaaacca cctaaaagaa gctgcaatac aagccgcaaa    6780
cagacagttt gaacagaagg ctacagatag cacgcctcag caacaaaagc ccgaaattaa    6840
gccacaaaac gagccaaaga cgaacgaaga agaagtttat atacgaggct ttaaagtcca    6900
tgtaacgaga aagcaggctt ttgcgcttgc tgagtttatg aatagccaca atataaagtt    6960
tgaaagtata tcaatataga cggtagccca atgggctac ctttttttgtt ttgtttgcaa    7020
tagtaatct attgttaaaa cttaaagttt cgcttgaact ttcaaataat gtgcttatat    7080
ttgcagtgtc gaaagaaaca aagtagtaac aattaaaaat taaatattat ggcaactaaa    7140
acagattttc agaagtagc aagatgtaaa acagaactcg gaacaacata cggttatata    7200
tacactaaaa acggatggta cgcttattac atgtgtggtt cttctatccc cgaatttaaa    7260
ggaactttag atgaagttga gaattacgtc cgttctgagt ggaatcttga aattgcaaga    7320
```

```
atggctaagt ttagaaacaa atagtaacaa ttaaaaatta gaattatgaa ggaaattaga    7380
tgcgttaaat gcgtatgtgt gattaataca gatgccgggt actatgcttc ttttgatggt    7440
agcttttgca gaaagtgttg gattaaacaa tcagatagat ttaaaagtga acaattgatg    7500
aaagcactct caaagagatt caaatgtaat attaacaaat agtttatttt aaaatggaac    7560
agtatttaga cttactaaaa gagactttga attatggtga aaagagatca gaccgaaacag   7620
gaacgggaac tatcagttta ttcggtttac aacgatctta tgatttgcgt gacggtttcc    7680
cgcttgtcac aactaagaag gtattcacga agggagttat atatgagctt ctttggatgt    7740
taaaggaga caccaatata aaatacctaa atgaaaatgg tgttcatatt tgggacgaat     7800
gggcaaagcc ttccggtgat cttggacgta tatacggtaa acaatggcgt gactggagta    7860
taaatagcaa gttaagagta gatcaaattg agtcagttat agatatgtatt aagtttaacc   7920
cggggtcaag aaggctaatt gttagtgctt ggaatgttgg agaaatacac atgatggcac    7980
ttcctccgtg tcactgcttt tttcagttct atgtgtctga gtccggttat ttggatttga    8040
aactgtatca aagaagtgca gacctatttt taggcgttcc tttcaacatt gcgtcttatt    8100
ctatccttgct gtctatggta gcgcaggttt gcggcttaaa gcctcgtaga ttcattcaca   8160
ctatcgggga cggacatata tatttgaatc acgttgaaca ggtgaaagaa caattgagta    8220
gagagccgtt cgcccttccc aaattggaat taaacccgaa tgtcgtaat atattcgatt      8280
ttaagtatga agatattaag atagtaaatt ataactgcca tccggctata aagggagagg    8340
ttgcggtatg aatgaaaaag aattttacag gtttttagcc tataataaat tggtagattt    8400
tgaaagatac cttcacatgg aatctgtata ttatctgaat aacttgctaa agaaaaccgt    8460
taattcgtat ttaagagatt gtatattgaa cgctataaat cataaattag cgggattata    8520
atttaaaagg gatgtgcaac gctttgccat ccctttttag tttctatata tcacataccg    8580
aaactatcgt tgctctatga aacaaatcta acaatatgta gtaacaagta tgaaagtgat    8640
gcaaatgtag gattttgaat ctattcgatg gttaaaacga tacgttttac atttcattaa    8700
caataaaatt aaagaatttc tttcgtatt taaagtttat ccttaacttt gcaacatcaa     8760
aaaagaagta gtaacattaa aaacgaataa tatgcagatt aaaaaagatc aaatttacaa    8820
attgcttgtg caagtttgca agaatgaagg tatttcattc tcctacgaaa aacttgtttt    8880
atctcttaat aagtacattg atgaagacga agaagattca gtattcgggt atgaaaatatc   8940
tgatattgat atttcaatcg ccaaacatat atcagttgat atttgcggaa cgcttgtatt    9000
aagcaatatt atttgccaat taacttgcat cggtgcggga gattgcccga attgcggagg    9060
tttactcaga ttgatagaat cttaccccaa atttagcaaa cagtattgcg atcgtgattg    9120
tgagccggag agagaagaag aaatgtata cgaatgttta acatgtggaa aggaggttat     9180
tttatgaata ttgaaaacac aatgatccga atcaatgatg cgattataag cgcacgtatg    9240
aacggcaaaa agattacgaa aaaggatatt gcagcgttgt tgtggaagga ctcaaagcaa    9300
agaacgcagg cggtcaacat gtctgccttg tgtaatcaca aaaccccaaac aataaaaatc   9360
gaatgggtga aagagatatg cgaggctacc ggagtcgatg cgaatttcct atttaatatt    9420
aaccctaaaa aataaagtt atgattaaaa atttaccaaa cattcaaaac gaaatgaatg      9480
ttcaaaagtc gaggtataac cagtttggaa aatacaatta tcgttcgtgc gaggatattt    9540
tgcaagaagc gaaaagagtg tgcggaaaat acggatgtta tgttatggtg actgactcta    9600
tcgaatttat cgaagggcgt ttttacgtga aggcaaccgc aaagattgtt gagactgaaa    9660
ccgggtctat tgaaacatgt tcggcttttt cacgtgaaga agatagcaaa aaggggatgg    9720
acttagcaca attaaccggg gcgacatcca gttatgcacg aaaatacgcc ttatgtgggc    9780
tttttgcaat agacgatagt atagacagtg attcaatgaa cggagagccg gaagcgaaag    9840
aaaaacgagca aaagacagcc tcaaaacaag ctaccaacca aagtaatact ggaagcaact   9900
caaattattt gggtgtgctt cttgaagaaa taaaaaaagc aacaacttat aaacatttgg    9960
gcgatattca caagaataac gctaattacc atcaaaatag tgagttcatg aacgcgtttag  10020
ttgtccgtaa ggcggaactt gaaaaggcgg aagcggaagc aaagaaagta taaataattc    10080
ggggggatgcg ttcccccaat aaaaaataaaa gcaatatgaa agaactaaca ttactcccca 10140
aattggttaa tgctgatgta acgtatatca gcgaaacaca tgaatatttt tcaagcgatt    10200
ttagaaagct gagagggata acgggttta tcaatgatca attattcc ggcaaacttg       10260
acaatatacc ggataatatt ttgagatcgg caactgagag agggaaagcg gttcatgatg    10320
aagttgagag gtcgacaaa gaaggtattg aaccggaaca ggtctacgga gagaactatt     10380
tgaattttaa agccggaagc ggtttaattc atatcgcatc tgagtatatt ctaactgata   10440
acgagtttat cgcatcaccg accgataaag tgtatttggg tggctctgat aaatcagtcg    10500
ttttaggtga cattaaaact acctacaaac ttgatttgct tatttgtct tggcagctat     10560
caatatacgc ctatctttc gagagacaaa acccaaattt gaaagtagag ggacttatcg    10620
caatttggct aagaggtgac aaggataagg acggaatttt ctctgttgaa cgcataccgg    10680
acagcgaaat agaattattc cttaattgct gtaagaatgg agttcgatat gcagacaatg    10740
caagcaaaga cagctacata gcaaaattgg aatcattgcc cgcaagagtt gcgcatatcg    10800
aagaaggcgt ttacgaactt cttgaaatgc aaaagaagat agacgagcat ttagccaagt    10860
tcaaagaaca gttgttaggt ctgatgtctg aggcgaaagc tgacaatata aaaggggaac    10920
ttatttcagt cacaagaaag aaagcgtata gccgtgaatc acttgattct aaagcgttga   10980
aagagcaata ccccgaaata tacgatcagt tcgttaaaac atctaatgtc aaagaatcaa    11040
ttcaattaaa agcgttataa ttatggttat aaatgaaagt ttagcgaacg agatcggttt    11100
agaggggtgcg actgtgtaca gctatgtatc tatcatccta tcaactgact tttataagga   11160
tcgttttaag ggatgccggg ttaaaggcaa gaagtgtaca gccttcatat caataagcaa    11220
gttaaaagaa ataattccct tcctatcgac aaagaagctg tacaacgcta tgaacttatt    11280
agtagatacg ggatacttaa aagaactacc attgcgaaaa ccgggtttaa atacaacccg    11340
atgttaccaa cttgttaatg tgatccaaca tttcgagtaa ccgataatac acccaccaa     11400
gtttttagt tgtgtgggtg ttttttgtac agcacgattc tgtgcagtat gtctataccct   11460
aattatcaga tatttgcaaa acaaagaatg ttaaatcata aaaaaataga tgttttccca    11520
ttgcagtata taataataaa cactatattt gcagataaaa atttaaaaca gtatgtatatt  11580
gaaagtagaa aacttagtta agattaagag ttatgccgat ttaaagggag ttacagtacc    11640
ttggatatgg aggcttatta agagaggaaa attagagtat attcaaattg atggtgcatg    11700
cttcattgag ttaacggatg aagaactgaa aaagtatgga gagtacaaag aacggataag    11760
ttcatttttg aatagcaaat agtattaatc attaaaattt tagaaaatga aagaattagt    11820
tttttaaagg agaatcaaat caagttttaa ccaacagctt attggtagct gataagttcg    11880
ggaaaaacca caagcatgta ttagacgcta taagagagtt aattagtagc gccgaaaaat    11940
cggctgtact aaaaatgtct gataatcaat gtaaaggata ttttccagat acatctgtat    12000
agattaatcg tggtgcaaca aattgagtat tattgtttta taatataaat agtatcaatc    12060
```

```
attaaaaatt aaagtttatg caagaaatta aagttttga aaattcggag ttcggaaaag  12120
ttagagtatc agtagttaac ggtgaaccga tgttttgcgg aaaggacttg gcttctgttt  12180
taggttactc aaacacatca tccgctattg caactcactg taagtcaggc gttgatgtgt  12240
tttgtgagca cgccaatggt ataggtggga ctaatgttag gtacgtaaat gaatcagatg  12300
tttatagatt gattatgcac tcaaaattgc ctaatataga gcgtttccaa gattgggtat  12360
gtgaagaagt tttgccatct atccgtaaac atggtgcgta catgacaccg gaaacgatag  12420
agaaagctct aacatcaccc gatttttatta ttaagttggc tactcagttg aaagatgaac  12480
aggaaaagag aaagcaagca gaggcaaaga tcgaagctga taagccgaag gttttgttca  12540
gtgaagcagt ctccgcctcg aacaaatcta tcttagtgcg tgaactttgca aaacttatca  12600
cccaaaacgg ttatcagatc ggggaaaagc agctatacga gcgattgagg aaagccggat  12660
acctttgcag ttcgggtgag tcgtataatc aacctacgca aacatacatg aatatgggct  12720
tatttcattt gaagaaaaca agcgttattt gtgacgggga agtaaggtt tataccgtta  12780
ccaaagtgac accgaaagga caaatatact tcattaataa gttttaggg aagggaatga  12840
aatgaaagta acaaggaata attatagaga gtattataaa aatactttta atatagagtt  12900
tgatagcaaa tttgaagtgc atcatataga cgggaataga gataatacca aaattgataa  12960
tttgttgttg ctgccaagtg agacgcattt taatttcat caaacaagta gattcttttc  13020
tacatttaaa gatgttagtc cggacttaat cagaatacag aaatcaagta catacgtgt  13080
tgaacaattg ggtatatata tttcttctat ttgtgagatt aagaggtttt ttgactataa  13140
gagatgtttc tatattgtgt cacccactgg ggttaaaaag aatagactaa aatgaatata  13200
ataacaagaa aaaggaatag caattataca actatttcaa acgtattttt acgtgatatt  13260
agattgtcgt gtaaggcaaa aggtattta gctgttataa tgggtttacc ggatgattgg  13320
gacttttcca ttcgtgggat actgtctata acaaaagagg gaagagacgc tgtatattcg  13380
gctattaaag agctaaaaga tcatggctat tgtgaagtgt ccgaacaaaa ggataataac  13440
ggtaaattta aggggtattc ttattgcttt tccgatgaag ctttattgca accgcatccg  13500
gaaaaaccgt atacgaaaaa accgcatccg gaaaacccga cacaattaaa tacttatata  13560
ataaaagact taaataataa tactaaatct actaacgtag attatagtat agccatgcac  13620
gaagaatctg ttttgttccc ggttgaaaag aaacctttag cctcagagat attcggcttt  13680
actgcaaaag ccttagatgt gactaagaaa gtgatagagc gaacagatag tttttcgat  13740
cagctaacat tcccgttcga gtcggaggaa tttaaaaaag ccttttatgt gctaatgacc  13800
caaccaaagt ggcgggtaaa gactaagact ctaacgcta tgcaagcaaa cctaaacgag  13860
attgcgcaat ttgaagaagg ttttgctatg ctattgataa atcagagcat atctaaagga  13920
tgggcgtcac tggtatacga atcaacgcca aaacagtata tgcaatggct acgggaaaag  13980
acgggagtct ccggaaatac acagcctgca aacaatacta aatcgtattt tcagagtgac  14040
gaacagcgca ggatgtatca gtcttatta acggaggact ttacatagca ttttaaggct  14100
taaatttcaa ttttaatcac taagacaata aaagtatcat gcatttggag aaaatcgaaa  14160
attcgggcgg aaaattagca aaatacgaag gttgcggatc gtttatagag aagaaccgaa  14220
aatttttatga aagtggcaac ttcggacagc tatcaaaagt agatcaaaag atattccgtg  14280
attcaacttt gcttttggtg tccgaatgta cagacgaaag aaaaagaata gataattttt  14340
ctaaggttct taacggagta tgtttagaga ctggtttaaa aatgccggat gtccgggacg  14400
caggaagtat attttatgct gtttgtgatg tgatagatat gtatttcgat gatctatcgt  14460
tcaatgaaat tcgtttggca tggcggttac ttgctgttgg ggaactcgac ccgttttgc  14520
caaaagacag atacggtagt ccggacaaaa atcactatg ctctcttcg gttgattata  14580
tttcaaaggt tctaaaggcg tataagaaac gaaagattga aacgatgaaa cgagtttcta  14640
agattatgcc ggacgaaaag ccaaaaccga caccgaaca ggaaaagatg ttttgaatt  14700
tgcaggcata caattttgtt ctcgcactt tgaagtataa gtattcggga cgtttccgca  14760
tagagcgtga caggataata aacgagtcta catttgcgta catggaacga ttgggatatg  14820
atatgtcggt atgtaccacg ttagcagaca agaaagagc tttgtttcaa tttcaaggta  14880
gacccgtaaa tagctttgcg caaatttcg aaaaagagtg tatttcgagg tttggggtag  14940
accacgaagc agtttatttt cgtgcggtac tgatagccaa gaaaagaaag ttattccagt  15000
attgggatga aatgttagcc ttttcaaatg aaggtagatag atcagaagat aatattgga  15060
agttgtacta ctacattcaa taaaaccaaa agttatgaat agaagaaaag taaaaagaa  15120
cggttatcgg ataaggctta caaagccttc agataaaatc gtttatgtct ctgactcgtt  15180
aacatacgaa aggagaaaaa aggagggaaa gagatgtta actctgtatt gcaaatatgc  15240
gtctattaac tatttgtgtg tttctcgaaa acaggcaaaa tctttaatga aagggttctt  15300
gttactatgg gaatagatat tatttgcgca attgatcccg gtgtgtcagc tggtggaata  15360
gtggtatata agccgggtaa tagtcttatt actatcccaa tgccacgcac ggcaaagggt  15420
atttttaacg tgtttcaaaa agtgaagcgt tccggtagcc ctgcaatatt cattgagcgt  15480
ctttcggttc gtgggggtga ctccgtaggc gggaaagaat ttagaatagc aactatgtta  15540
gagaactaca actaccttgt gtattgtgcg ctcgttcttg atattccttt attctctgtt  15600
gcgcctattt cgtggcaaag tggttaaat ctgagggaga aaggagagaa agaggaaaag  15660
aaggatagaa aagaaaagta tctgatttat gcgatgaagc aattcccact cgcaaacgtg  15720
aaaattatgga atagtgacgc tatatgtatt ttgcgcttcg cacaaatgaa gatgatttgt  15780
gatgtcgatt ggttttcaag taacatgcag aatgaaaaca gcacagaaat aggattttct  15840
tctcctctgt tggacgatag tattaaattc gtagaaagat atggattcaa aagaaaacga  15900
tctaaaaaac gctctaattg aatcggtgaa agagctgaga agcgcacaga agcgatttga  15960
gcgattcggt gagagataca gagagagaaa agaaaggcg gaaagaaag tagatgaaat  16020
tctatcggtt atcgaagata agcagttatc tattttctaa caaagtttaa ataacggta  16080
tttcggaaag atttacccgt tttatttgt gtgaatttaa agttttgatt taatttgcag  16140
cgtagaaata aaacagtttg taacataaaa tcaattaatt atgcaggaaa ttagcaaaaa  16200
attaagtgaa cagtcagtag gaacggtttt ggatagaccg gagtatagaa aagagctttc  16260
tatttattgg gatggcttaa aagagcaacg ggaaaaggta tctttccaaa tattgaggaa  16320
tggcggcatc cctaaaagga taacaataga cagagttggg agaatggatg cagaccaact  16380
tgtgtcagaa ttcaagctaa tacttgacag aaagagtgag ttgcctgcaa gtctgaggca  16440
ctttatttcg gatgtatgcg gaaagtgtt tattagtttg tttacaaaag tgatcgaaga  16500
tgaagcaaaa gaaaataacg atacccggga aggtaactaa ggacggtaag ttatccatct  16560
acatgggaga gcttaacgag tttatgaaga acaacgcagg gaaaaatatt attgcggagt  16620
ttacggtatt agaccgtct gattcttcat ccttgcgtgg atactacttt aaatacgttg  16680
ttccccaatt tcagaaaggg atgtgcgaaa atgggtacag gtggagcgaa gaagaaacgg  16740
aggcttatat gcgtagtatt tgccctatta cgatgggtga agttgtagat attgaaactg  16800
```

```
gtgagtatag aaaggactca gttaaagtaa ccgatttaag caatagcgaa tttgtcgaat    16860
acatagaatt tttaaagcag tttgcggcag aagaatttag tatttatatt gaagaaccaa    16920
atagatttgt aagatgaaag aaaatgaaga aatgacttta gaggaaaagt tcaatttgat    16980
gtgcgaagcg ttaagtatat caccggagag aattatagat agggatatta cccgttatgt    17040
atcacttcga agaaattgca ttatccatca gcttacgcc tataaaaatc acggtttacc     17100
cgaattgata ggtcgcacga aggttttaat tatgaaagcg catgaacgtt ttcaaggcga    17160
attagatgtg aaagatatga cagccgtaga gttttgtccgg cttatagacg aacgactgca   17220
aaagtatatt gatggcaaag aagattaaga atcttgttct tgttcattgc acggagtgta   17280
ggttcagttc agatcacaat aatttgattt gctattgcaa aaagagagat aaaaagttat   17340
gcagttgccc gaacattggg cgggtctgtg agttttacat taaaaaataa agtatcatgt   17400
taaaagacaa ttttgaatta aagagagtta agttcttgaa taacggttta gaggttgatt    17460
acaatgattg ccgtttggtt gatggtgaag aaacaaagac gtttcacaag gtaaaatgcc    17520
ccgaatatcc gcatagagat ttaggaattg cggcaaatga gcttcgttca tacatagttg    17580
aattgatggg aataatgaat tttaggaaca tcacctattt gtctgatttg gcaaaacaag    17640
acaatgagtt aagtagacaa ttcgatgaat attttgaaac gcttgccacc cgtatagcga    17700
ttagcgagat agtttacgat cccgaaaaga atacaatcgt tttcaaatac attttcacag    17760
gcgtagattt atcccggttg aaaatgcaaa cgagcaaaat aatgttggac ggtgaggggt    17820
tgaaatttga aatagcacta caagaagatt ttgaagcact gaaagatgaa attttcaagt    17880
atcttttttga gaataagcgt gcacaattgg agctattcgg tgagacagca acggcagaac    17940
cggacgatag tttaacgccc gatgatgatt tagaaggtga cgatatgttt tttgatgatg    18000
aagaagcgga gcagccggag ttgatcgaag aagatgtaca cgattgatac gtttgaggaa    18060
atagattatt gtttaagcat ggggtataac ccctgctat tcaataataa tttcgatatt     18120
gagcctaaaa caaggtatga atatttaaaa cggatgttcg gagagggtca cggacagagg    18180
gaaaatgaac gtttcttccg gtatatgtgg gatattaagc ctcactattg tgaagaatgt    18240
ttaaagccgt tagcagggta ctcagccgtt tatatttcgc atattataac gaggggatcg    18300
aacccaatga ttgcgcatga tcctcgtaac ataaacatac tttgtttcaa ttgccataat    18360
cgttgggagc acgctaacac ccggaaggga atgcggatat atcaaagtaa tttagaaaaa    18420
ataaaagtcc tcaaaaggga cagttttaaa ctgcaaaaga aatgaaatta gtaaaatttg    18480
aaaacgaggc tggaaataaa gtaatgatta acccctaaaat ggtagaatca ctattccaat    18540
atagaagaga tttagtatac atgtatacag taaatcagaa aaaccccctac tgtgattaaag    18600
ggaatattga ggaagttaac aagaagttaa ccgaaggtag caagattgat tcaatagccg    18660
gacttatggt tatcgtcttt attggaattt acatattatc aacattagca aatttattat    18720
cgtaatgaac ttaaacaaaa tcgaattgat cggtcgtgtt tgtgctgatc cgcaagttaa    18780
aaccttcgat aacggaggaa aagtgtgtaa cctttcgatt gcaacaaacg aagggcata    18840
taaaacgagt aacgggatcg aagttccgga aaaaacagac tttcacaatg taacattcaa    18900
aggtaaattg gctgagattt gcgggcagta tgttaccaag gaatggagt tatacgtaga     18960
gggcagtttg cactatcgta aatataccga ctctaataac gttgaaagaa ctatttctga    19020
gatcgttgta aggtctatgc agatgggaag aaaagcaggt gagggaaacc agccacaagc    19080
cggaggcaac ggaaacaaac agacgccaac cggaggttat agcggtcaac agcaaccgcc    19140
tcagcagatg tttacgcaaa atgatgattt gccgttttaa ggtgatttct aaattgggga    19200
tgtatattgc atcccctttt tttgtgttaa atacatgtta aaacttaaag tttcgcttgc    19260
agtattaaat attatcctta tatttgcagt gtcaaaagga aacaaagtac taacatttaa    19320
aaataaatat tatggtaaca atgacatcaa aacaattttg tgagagaatg tatgcaattg    19380
ataaattact tggtgggagt gagtccggat gtgctcaatg ttcaaacgat agattttctt    19440
gcggatatgg aaaggagaat acggttttaa ccaatgcact tatgaaagcg tgcgataatc    19500
acaaagttcc ttataagata gaagcaaacg aatattgtat caatttcgta gtagaattta    19560
aataataata gcggtagaaa taccgcttta aacttatagt tatggaaaga agaagattat    19620
ccggtcagta caaaatagca atgtacaaaa acatagggaa tgacacgttt aagggagtgg    19680
taagaacggt aacaggtttc atgtatcagt gtggtgcata tcagtatttt acttattggg    19740
agaatgataa taaaatatcg gttacagaat caagtacagg ttttcgtgca atgtctttgg    19800
atgttgaaaa gggagaaact cctaaaacta cgcatgatag gatagtttgat aagttgataa    19860
gttttgatcc atcttagaa aactggaata gtgctaaaga gatgatgaag aaatataata    19920
ttccatatcc tcttaatgaa tggatagtag ggctaaaaga cataaccat gaatgaagaa    19980
gtagagaaag caagatcgt gagtaacgaa gttatttcgg aaactatcag aaaatcgaat    20040
gagaataaa aggcaatgga ggacgatttc agattagtaa gaaagaagtt gcggaaaatt    20100
ggcgatcgaa taaaatttga gagaaagaaa cttgatatat acaacgaaga aataaaaagg    20160
agggttaagt atggaatttg gtaacttact gttagataga ttgggggttta accgtgaaat    20220
gttggaagct aaacttttgg aaatatccac taaggagaaa gagataagag ttctaaagaa    20280
agaagtttcc ggtataatgg atcacatatc aaaattggaa agtacgttaa atcttggaaa    20340
gcattattat tgcggtgctt gctgctatct tgaaagtaaa tgcaataagg ggaaatataa    20400
gtgccttgaa accggagaat acaaggaata tcactgtaag gcgtgtgaga aatttagaga    20460
tttaccattt taataactaa ttataaatta aatattatga ttgattttaa tcaaaaaagt    20520
atctgtttaa ctaaggagtg tgcagaacag catgaaagaa tgaaggcaaa aggttttat     20580
gactcagagt tttttgagtg taaaaaatgg gcgttgatag tgtctgagtt ctgcgaagct    20640
atggaggcgg aacgaaaagg gaagtttgta gaaaacgaga tttacgatat tgttttaggg    20700
tgtgaggaag gttttgaaaa tgtatttaaa cagtgcgtta aagcacagt tagcgatgaa    20760
ctcgcagacg tgtttatccg gtgtttggac gcaataggac attctattga taaaattgcg    20820
tgtcctaccg aaattttcgt ttttcaaagt atggttagcg atcattcaa taggttattg    20880
tatcttgaaa aatctatttc atcaattgtt tattatgcca ttcaatttgt accgaaatct    20940
gtatttggca aatcgtgcat taccgagtat actaacatga tggcaataac cattgcagcc    21000
gcaaagcttt ataacataga catatctaaa gcaatagagg caaagataag atataacgag    21060
ttgagaggtc aaaacatgg gaaacaatat taattcatta tggaagaaaa aattattgat    21120
ttagcaagaa gaagcgttta ttgcggtgat ccggaaggtt atcaagttgg gggatgccat    21180
tacaaggcgt ccggcatgca gcttctgaaa ttttagaaa agaataaagt tggtttcttg    21240
gagggggaacg caatgaaata tgtgtttagg cacgataaga agaacaaaga agaagatctg    21300
ttaaaggcta tccagtatat ccagtttatt ctaaagtaca gatatggcaa atacttagta    21360
ggtgatacgc tgtttagtga ggaagaatat aaaaaggcga ttgaacttat tgaaaaacaa    21420
gatacgattg aacttgatac tactttatc cgaaatgcgt tgaaacccca atcaattgtt    21480
tcgcctaaaa tatcggtaga caaagcaact ttatatgttg caaagctaag agaggttaaa    21540
```

```
gccgaatata tcgaaaattt tgttttgtcg gatataaaaa aatgcaagct tttagatatg  21600
ggactacggt atagtgcggc aggtggtatc tatgttcgtt ttgattctaa gagaggagaa  21660
acaatatgtg ttaagccggg ttattatgtt gttctaaatg aagatgggag atatgaatca  21720
tactcaaaag aaaagtttga gtctactttt caacccaaat actaacaaaa ataaataatg  21780
ataggtcacg ttgcaaatat agcagcgtga ctttatttt atattatcta taatagtgtt  21840
atttttgcgc atattgaaag attatataat ttgtagtaca atatacagaa tagaaattat  21900
aacttaaaaa atacgtctta aaatggataa aaaaataggt tcaatgaaaa gagggcaggg  21960
aaggcatagc cggacggacg aacagactga agagaccgt tcctttgcct ctgatttgtt  22020
tttgaaaggt tattcttata gaagaatagc ggaagcgatt aacgagcgaa ataaggcgga  22080
tgaagtgccg tataccgtga cttatcaaac agtgtataat gatattcagt tttgcctgac  22140
tcagtggaaa agagaacagt tcgataatat agatcagtat attacgcagg aactccaatc  22200
tttgataat gtggctcgtg aagcgtggga agagtgggaa aagtctaagc gtcccaaatg  22260
taagacaaag tatattttag ggaaggctaa ggaggtgcaa aaggaaacaa caacgggtga  22320
tccttcttt ttgaatgtag ttctcaacgt gcagcaaaga aaagcaaggt tgttggggta  22380
tgactcaccg ttatgtataa acttggtggg agataaagaa aaggaaaaac ccaaatacga  22440
tttttcggat gtcccggagg acgtttagaa acaattggca gattctttgc aaaatacgga  22500
gggtaaaaag tgaaaaagt aaatgaaata ccaccggttg agattgtgaa gtatgttgcg  22560
aggaagaagt ttaagaacta tgccaaattc atagatgata aaagtagttct gagtcagttt  22620
cacaaaacat actacgagat tctcgatagg tttgcacatg gtaagatcaa aaaactgatc  22680
gttacagtgc ccccacaaac tggaaaagaa ttaagtgata gtacattagt acctacacca  22740
acaggcttta aaaggcatgg agatttaaaa gtaggtgatt atgtgttggg cagattcgga  22800
caacctgtta gggttctttg ggtgtctcca aagtgtcagt ctcagtatgt cgttacgttt  22860
agtgatggta taaagttga atgtcacggc aaacatgaat gggtagttta taataccaaa  22920
aaacacggta gaccattaga aaggcttgaa actgagtata tgtataaaat tggtacatgt  22980
agaggggaga gaaataagag aggctctcgt tttaattttc aagttgatgg aggtgttgta  23040
tctcaatttg agagtcaaaa agttccgatt gatccatata cttaggtgc atggttagga  23100
gatggtgata tgaatagtgg tttaattcat attggttgca atgatgtttg tataataaat  23160
aatactcctt acgcatttca cgaaaataaa ggaagtacaa cgaggcgttt ttattcaagc  23220
gaattgtttt ctattttaaa aaaagagggg tttatcagaa acaaacatat accggagtgt  23280
tatctattta actcagtaga tgttcgtaaa cagatataag caggtttaat agacacagat  23340
gggacggtat ataaaaaaaa tggacgtgtt acgatagcta atgcgaataa aaacataata  23400
gatatggcaa ataaaattct ttatagttta gggcaaaaaa cagccatcta tgaagaagag  23460
ccaaagttat ctacatccgg tattcaagga aagctaaagg tttatcaatt atgttttaac  23520
cctactatca attccccttg taaggttgaa agaaagaaat ttgttaggct tgttaaaaat  23580
aggcgtagag ccataacaga tatagaaaag gttgataatt tgggttgggg taactgtata  23640
caggtcgaag gtggtgttta tttggtaggt gagacgtttg taccaacgca taatagcgag  23700
ggtagcagta gaaagctacc ttcttttcctt tggggctta acccgtcttt aaagatattg  23760
atcggttctt atgccgcatc actcgcgagag ggtttaata aggatgtaca aagaataatg  23820
gatacaccgg agtataaaag cctattcccc gacacccgaa taatgggaga ggaaaaaaaa  23880
acgaggtatc aagcatttgc gagaaactca aaaatgacgg aaacaatcgg gaagggtggg  23940
tatattat ccgttggtcg taatggtagt ttgacgggta aatctgttga tatagcaatc  24000
ttggacgact tatataaaga tcacatggag gcaaattctc cgattatccg ggaagctgct  24060
tggaaatggt acaccaccgt tgtaaccacc cgtctacaca ataacagtca acaacttatt  24120
gtgtttacga gatggcacaa ggacgattta ataggtagga tcgaagataa agagaatgtt  24180
gtcaatgttg aaaagtggga agatttggat aatataccgg aaggcgcttg gattaaaata  24240
aactttcctg cttttaaggt gggagaacca acagagattg acccacgttt gccgggtgaa  24300
gcactttggg aagaaaaaca tagtgctaaa aaattgaacg cacaaaggga acttgataga  24360
aatgaatttg agtgttttgaa tcaaggaaac ccgggtagcg ctgagggtac tctgtacggc  24420
aactttaaaa cgtacaccga taaaagcgat tttggtgtgt tggtcggaag gggtaactat  24480
acagactgtg cggataccgg tagcgactac ctttgttcaa tttgctatga taagtatcaa  24540
tcaaaagaag cggtttggaa tgaaaaggaa aggaggtata agcatcttat tttctgcctt  24600
gtcactgata ttatttatac gactgagcca atagaggtta cgcaagtaag tgttcccgac  24660
atgctaaata gaaatgatac agattatgca aatatagaaa gcaacaacgg agggcgatct  24720
ttcgctgtta atataagccc taaaccaag actgaaataa attggttctg tcagaagtta  24780
aataaagagg ctcgtatatt gtcgaacgct gcaaacgtta ctcagtctat tgttatgccg  24840
tatgggtggg agtcacgttt cccgaaattc cacgaacata taacaaatta ccttcgtgaa  24900
ttttcagcga ataagcacga tgatgcggca gatgttttaa ctggtatagt cgagaaagaa  24960
gttattccaa ctatatatca aaaaagaaga ggaataaggg ttataaactg ataaagtagg  25020
aaaatgtatc agactttcaa gtttatacgg tatatttgca aagtaaaatc aattgtttaa  25080
ctaaattttt ataattatgt tgtattgtga ttgtccttta agagcagaac ttccggatat  25140
tcccgcattt agctgtcccg aaaatttcgg gcaagttcaa aaacttgctt ttcagagact  25200
cgaaaaaacg gcaggaactg caaatactat gactgccgaa agtatcgcaa agttggctac  25260
atggactccc ctactgtcag caaaagacgg tactaaagta gtagttacgc cttatattta  25320
cgagccgaca gtagaggcgg gcgctgccct tacttatgga ggcggaaacg caactccgga  25380
aggtattgta gaaattttag ggtcggagtc gacaccgttt acagcttcgt tcaagaagtt  25440
gccgcaaacc attattaagg cgatgaaagc gttaatgtgt gaagcgggtc aaattggtgt  25500
tttccttatc aacggtaacg gacaaattgc ttgtgataag acgggtagta atttgcacgg  25560
tttcccggtt tggtcgctgt ttatcggtga taagactatc ggagattttgg aagctccgga  25620
tagcaatgct attacgtgga gcttcatgcc taattgtcg gacaacttca ctatcgtgaa  25680
acctgagttt aaccctctga ctcagttagt tcctgccgta agtccgggtg taggctgatg  25740
atagctaaaa aaacgtatat ttccctcagt tgtgaagaac tggggaaaac tcgtttattc  25800
gatattgaac acgctgagag acttttggga atggttaaca atggaggtg gcatataccg  25860
gaggactcag aatttaaatt aaatgaaaat gggaaaatca ttagacgaaa taaggagat  25920
atacagacat ccggagggga tcagtcaaat agcgaaagca aggaaaacac aagaaagaat  25980
agcgtttcac acacgggtga gaacgagtga tgatcgtaat aagccagtaa ttgactttct  26040
ttctaaggtt aagacgtgga tagcgaaaga taaatatgat atttttcctat ctatgttcca  26100
tttcccggtt aaaacaaatg gtgttacttc tgagatattc gacaaactga gccgtgtttt  26160
cgatggtagg aatccggttt ataactatca gtttaaatca tctgaggatc gggatgactg  26220
ggagtattac cgaaaggatg ttttaaaaga accttcggtt tggagtacgg acggttggga  26280
```

```
taatttcaag catagaatta actctgtttt ggtcgttgat atgccggagg tacaggtagg  26340
agaaaaacca gagccgtatt tttttggtt gcctattgca aacgtacttt cttatcgcac   26400
atgtgggaaa gactgtaatt tgatggctta tatcatgtac gtaacggacg aaaataagat  26460
cgtctatatt gatgaagaac gttatgtaag atttgataaa acgagggaaa acgacttgat  26520
tttagaggta gacaatatgc acgatttggg ctattgtccg gctcgtttct tttggtctga  26580
ctctatatca ttgagtgaac ccgacattaa aataagccct ataacgagcg aactcgactc  26640
tttcgactgg tatctttatt attccacggc aaagaagcat ttagatttat acgcatctta  26700
tccgatttat tccggttatg aacgtgattg tcactatgag tcacacgatg gtaaagaacg  26760
gtgtgatgat ggttttttaa agaacgaaaa aaacgagtgg ataacaggtg cggacggaaa  26820
accgatggcg tgcccgattt gctcaagcaa gcggttgagg ggcgcaggct cttatgttga  26880
gatacccatc ccggacgaaa tgcacaacgt ccccgacttg aaaaacccga tcactatgct  26940
atccgctgat accggatcac tcgaatataa cgtaaacgag gaaagagggc tgagagagga  27000
acttgtaaga tcggtaacag gtggagaagg ggaattaaac aggtctgagg ctattaacga  27060
aaagcaagtt aaagcgggtt ttgagtcctt gactactaaa ctaaacagaa tcaaacgagg  27120
cttcgaggaa gcgcaaacat tcgtagactc tactatctgt ttactccgtt atggtagatag 27180
cttttgtttct tgcaaatatta actacgggac tgagttctat atctatacac cggaagagct 27240
ttcagagcgt tataagatca tgaaggaaac cggagcgtcc gaggcggaac ttgatgcact  27300
gaggcaacag atcatcgaaa cggagtatcg gaacgaccct acacagatgc aaaggttatt  27360
aatccttaac gagatagagc cttattcaca cttaacgaga gaagaagcgg taaatctgta  27420
taaagaaaac gttataagtg aggaagattt gcgagttaaa ttaaaccttc ctacatttgt  27480
gcgtagattt gaaagggaga acatgaatat cattgagttc ggttctgcac ttgactataa  27540
aaagaaaatt gaataattaa ttaacacttt aaaaaagtac gcaaatggtt tacagaacgg  27600
atcagttaga tcaactgaat gaaagtaatt acgtttgccc gcaggatgaa gttaaattgt  27660
atcacgttat tcaagaagtg aaaagagttta acccgaaaac agggcaaaga atcagcgtcc  27720
cggtgttgca aaaatacaag cgaaagactt ttgaacttga tattttaccg agactgccaa  27780
gattgggtta tacattgaga gttgtttttcg acccggttaa atatgaatct acaatttgtg  27840
aggcaagacg agccgcagaa ctggcagcga gagccgaggc aaaaatgaag gcagacgaag  27900
aactgagaga gcaaattaga cgtgaagaag ccgcaaaact tcgtgcggag ttgaagaaac  27960
aaaaagagaa aggagaaaag taatgttaac agtagatttg cttagacaga ataaagcgtt  28020
atcggagcta tcggatgaag ttcttaacgc tatttcggaa cttcaaaaa acgatgaagc  28080
gcagacggtt gcggcaaagg tgagagaaac cgaaaatagt attgctactc aaatgaagga  28140
ggctttcggt attgaaggtg taaccgatct cgatttgaaa accgcaattg agtttggcaa  28200
aacaaaactt tctaaatctg ataccctcagc ttttgaaaaa cagattaacg atctgaaaga  28260
agaactaaaa gctgagaaag ctaaaaaggg aggcgaccgg gatactgata aaatcaatca  28320
gcttacagcc gaactaaacg acaccaagca aaaatttgct ggagttgaaca accaactttc  28380
agagaaggaa aaggagttta acggtaagtt gaacgattac aagatcactt cttacatttc  28440
aagcgcaatg caggggatga agtttaagaa agatatttca gagccagttt taaacgttgt  28500
gaagcagcag gcggttaact tgcttaaaac tcaattctca ccaactttgc aaggtgacga  28560
aggttctgaa agtcttatct ttatgaaaga cggtgttact tacaacaacc ctgcaaatag  28620
tctgaaaccg tttaccgcat cagaacttct gtctcaacag tttgaacagt tcggtgttct  28680
tgacaaaggt agacaggcag gaggtgcggg tagttccgga ggcggacagg gtaacgtag   28740
cttgcttgat ttaagcggtt gcaaaaccaa agtagaggca aacaaggttg cgcaggagta  28800
tttagctaag aaaggttata caagcgagtc ggaaagtat caaacggagc ttgataaaat   28860
ttgggttgaa aacaagatcg cagatttgcc aacagaataa ctaaagaggg gtttaaaccc  28920
ctcacaatat aaactttaaa acaatagatt tatgtcgtta attgctacaa ggacacagga  28980
gtttagatta aagaaccta acattgacaa aaatatgtct cgcatgaccg agtgggggtgc 29040
gtatgacttc ttttttgtctc aaacaaatgc gatggactca atgcttttccg atgaaactaa  29100
gcgtagagcg ttcgcctcaa tgggaagtga tattaagatt cccgtaattg attacgataa   29160
aaacgtaaca gtgtcaaacg ctcgcacatg cgttatcgca gatgcggaaa acacttcacg   29220
tttgatcggt gtaacgtgga aaacctatgc tttcggcttc actatgacac cgaacatgta   29280
ttcaaacaac gaaatcgatt accaacagga ctggaacaga aagctacaaa agcacatccg   29340
taagttcatg gataccgttg ataaggacgc tattgcggct ttggaggcaa acaaaacaca   29400
ggtattcgga aacttgctgt attcacacaaa acgggtaaca gatgtgcaag tgaaattcac    29460
tcagcgcaac gacatcctca gcgacttgca cccgatgttc cgtgcaaacg actattccgg   29520
tcaactttcat atcattggcg acactggttg agactcgtaac ttgcgtaaac tggaacagca  29580
cggtttgtac aatgacgtta acaaacagtt ggagtatgca aacaaagtgt tccatttcac   29640
caacaacatg acttttagagc cggaaaaactt cgctcagatg tatgctgttg aatcgggcaa  29700
cgttggtttg ttgaccccgtg tagaccgtgc agcctacaac aacaccaagt cgggcacgca   29760
tgaatttggaa aaggttgttc ttccttattt cggtaaaagag gttgaaacac actactacga   29820
agaggtaggc gatcagtcag ctatcgcagg cgcagctact gccgatatga cttgtgacgt    29880
taaacatttc tacggtttct cagtagatat tgctttcgta gtagctttta actccgatcc   29940
tgtaacaatc gctaacccga ttatgaagat cgaagtaaac aaagaaaatt cagaatttgg    30000
aggtactccc gtttacatca cgaatgcgtc tcaaatcggt ggaggttctc cggctggcga    30060
attatcgtt aaccttcta aaatcggagg tagtccggtt ctgtgaatctg ctttgaaagt     30120
agatttggat aaaagtcaaag gtgcagcggt ttcggctact ggtggcgtag ttggtgttaa   30180
agtcaatgcg caggctgcaa atctgaatgt tgaggtgaag aactcaacag attcaccgtg    30240
taacacaaag gaagttccgg gagagtaacg agaaagtaaa ctaagtatta acaaagggag    30300
ggggacaaaa tcccttccct ttttttattt ataaccatgt acagattaaa ggatatacaa    30360
aaagaacttg ccacgctcgt aggatggcgg cagtcgtacg atagagacgc taagatagac    30420
gaaagtttaa cggtgtccga tagtggtgtt atgtttcaag acgttcaccc gcttgtgacg    30480
ctaagaaaca ttgaatctat tatgccactt gattactatt tacgttatcc ggagtatcgg    30540
gataccgaca cttataagcc gggagacaag gtagtttacg gcaaggacgt gttaacgctt    30600
cgtccggacg tatgggaggc aataacgaga atgttggtg tagagcctgc cgatggtgat     30660
aactggaaac ggtacaaccc agtacgacct tatttgcgtg aattgaacga aagagcgatc    30720
actaataccg ttactcgctt cattaatgaa aagttgattg cagggggaaac aaagacgctt    30780
ttagagcgta caaacttctt cgatggttcg gggaagataa ataacgagat tgaccctacc    30840
gatagtattg taggatatga aatattgcca gtccgttcta tgggagtaac agccaagatc    30900
gagaagatag gtttgcagtt taacaagccg ggaagggtaa aactttacct tatgcacacc    30960
tcacaggtag acccgattaa gacgttcgat ttgaattata ctaaaaatgg ttcttatcaa    31020
```

```
tggtttgatg tcggtaacga tgtgttactc ccttatatgt ctgaggaaac ctcacccggt   31080
ggcttgtggt acttgtgtta cgatcaaaaa gaattgccgt tagggatgta tgctataaac   31140
gtctctaagg acttttcacg tgacccgtgc ggtacttgta atattggaag cgtgcaggcg   31200
tggagagagc taacaaagta tatcagagtg tcaccgtata gagttgactc tacgcagtcg   31260
gaggatggcg taaagatgtg gaatatagaa atgaacatgt atacgtctgc aatctgctac   31320
ggtttaaacg ttcaattgtc ggtagggtgt gatataactg actttatcat tcagtctaag   31380
tatgccttca cgcatgccgt ttccctgcaa atggcttctt atgtgctgcg agaacttgca   31440
ttaaatccga acgtccggca aaatgccaat caattgaata tcgaccgtga aacgctattg   31500
tacgaagttg acggaaactc acagggacgt gcgcagggta tcggatacga actaaagaag   31560
gcttttgagg ctcttttctat tgatacaaaa gggatggata gaatatgcct ttccttgccgg   31620
aacaacggga taagatttaa agcaacatga taagcggtct aatagataag tttaaaaagg   31680
taggtgagga actcgacacc ggagaaatag caaaaaagat tgtgcgtgac aatgataata   31740
tacttattga catgaacgca caggatcagc tatacgcaaa gggtgttaac cgtttgggcg   31800
ttcgtataga tgaataccaa ccctacagac ccttaactat aaaggtcaaa atagaaaaga   31860
ggcaaccgta cgaccgggtg acactaaaag acacaggaga gttttacgac tctttttatg   31920
ttgagacagc agaagatcgg ttttacataa aagcctcaga tgaaaaaact aattggctta   31980
tcaaaaaata cggtgctgaa attttcgggt taacaaatga ttcacttgct gagtttatta   32040
acgattatgt gaaggacgaa gcatataaca gagtaaagga gatattaaat gaacgatagg   32100
gctataatta gaccaaatgc gacacttttc gataaaacga tagccgatgt acaagtaagc   32160
ctaacaaaat cgcttaaatg gcttaatttc gctttcggga acgtggttaa attggtagag   32220
agaaacgaga gggggaaatt tgttacccca tcagtgtatt ttaagggaaa tgattatttg   32280
cgcttagaac cggacgataa gcggggcaac gtttgttttt tctatatgca cgactcacaa   32340
gattatgaag ggggagactc tttgtctggc tttggcgatc tgaggggggac ggttagcatt   32400
atcttttggt tcgatacccg taaaatcccg ggagcagaat attacaacgt ggagtttgta   32460
aagtcagaaa tactgagagc cttaacgcac gaactttatc ttccatccgg tgatatacag   32520
gtgagaaaga tattccacga cgccaacaac gtatacaagg agttttctat ccaaaagacg   32580
gagaatcaat actacgttta tccctatgcg tgtttgcggt ttgagtgtga tattcattgc   32640
gaagaagggt gttattaaag ggggagtttc cccctttttt gtgttaaata tatgttaaaa   32700
cttaaagttt cgcttgcaat attaaataaa gtccttatat ttgcaatgtc aaacaacgaa   32760
agacccaca atctaaccaa gacgcaaaaa gattgttgaa agattaaatt cataagagta   32820
gaaataagc aacggtatct acgaaggggtt aaatgaaggt tcggtatccg attaaatgaa   32880
gctataaagc ccaaatcttt cgatgaatga caaagtagca acaattaaat aacaagatta   32940
tgacaaaaga attattcatt cagagaacag ttgaaaaatt tattatgatg gaatttatta   33000
agggaaacat ggataccaaa gaacaagttg atacaatgat agaagttatc aaaagaaagt   33060
tagacttttc gcatgatgaa gcatgtgatt ttataagaaa agcgatcgga ataaacgaat   33120
aactttaatt attaacaagt gggggtatta cccccacata aaaattaaaa atatgactac   33180
ttacatttat aaaggacaaa agataagcca ctccaaaata ttatccctat tgcgtagtgc   33240
aggcatttac ggaggaaaca agctatcaca ttatgaagcc ttagttaaag catccgaaaa   33300
cggcaacgaa agagccacgt atattttgag agacttaaaa gtgatataat aatcgttgga   33360
aaccacacaa attttaaagg tatgtttaac aaagaaagaa ttgagaattt agaaaagaga   33420
gttaaggaac tggaaagaat agaaggtatt tcaaaacttt cggaagatgt atctaaaaga   33480
cttatacatg ctttaattga ctctaacaac gaagtagtaa aaagagtttt tgatgatgtg   33540
tgtgtacgtt cgatatatgg tacatctgtg tttcagccac ctaaagccgg agacattcac   33600
gcaagtaatg cggtgtttaa cggtataccc gattctttaa agaaggtaga agaggataag   33660
gcagaagcac ctaccattgc aagcgtgttg gaaaaagcaa gaaggaatac gattgcgata   33720
caggagcttt taaaacgaac aggatgttcg aacgtgaacg aagtgataag caagtttgaa   33780
cttggagttt ctttcaaaaa gatgtatgat gaagaagcac gcaaaagaaa agagcttgca   33840
atacaaagag atcgtttaga aagcgaaatg atgcgtcaaa tagaggaact aaaatcaaga   33900
agaaacgagt tgttagcggc aacagggtgt gcaaactttta gcgacttgaa aaataaattc   33960
ttatgtaagg atataaagag ggatgaacta ataggagaaa taaacgagct tgcacggcaa   34020
agagaatttt taaatcgtga tttaagcaat caaatagcta aactttctga taaaaaccaa   34080
tctttgatgc aaagtgaaaa aagccttatt tgcaaactcg cagataagga ggtagaatta   34140
aagagagcgg aagaactttc agacggtaga tataaagaaa tcgtttggct tcgtggcgaa   34200
ctgaaaaatc aagaacaggc ggtagaaaaa ctaaagacg aaaacaaaca gcttaaatat   34260
gctaattcga aatggcaaa aagaacggtt gattctattt gttcagaagc ggatattgcg   34320
gtaggatatt caaatttgca aaagagatgt aaggatttgg aaagagataa aaaatcattg   34380
cttaattccg agagagaatt acaaaaacaa gtatttgacc tttcgagaga taaaaaatac   34440
ttggagatgc caaacactgc actcctgcaa gaaactcgta aaattagaga gtctttgaac   34500
gaaagaatta agaagctaag acagagactt aaaaaatcgt ctatccgtta cagagactta   34560
aaagaaatca tttcgcaaaa cggtttgaaa tcaatttaat ataaaatgtc cggtgttaaa   34620
gccgacttaa aaaataaaac attatgaaag tagtaaaatt gagaacgttg aaaattgaac   34680
cggaaatagg cgaagaggta accgttaaaa caaatgaata tacttactcg tgtattgcag   34740
agaaaatcaa agacctttca tgtgaggggt gtttatttga tcgcttacaa aagtgtgaat   34800
atatcgatg ttccgggcgt tttagaagag atggaaatga tattatcatt aaatgtacat   34860
caaaaaaaag aagggaggtt gaaaatgcgt agactatcta tatcagacaa aggtatgttt   34920
attccggaag aaggggaaat attttttgcg gaagtaccaa ataaggggat agatcgaaaa   34980
gtgaaaaacac tggtatcgat agacgataat ccatgtgcga aatgtgcctt tcgcatggg   35040
ggactcggtg cattgtgttg gagtgtgatg tgccttgaag aaggtgtaca atatacatttt   35100
aggagggtgc acgatgggaa aatttaaaag cgtagaacta tatgacacct tcataataga   35160
tcacccagtg acaggggaaa cgataagagt gcaagcaatg gaaggtaaca atgtaatatc   35220
atgcaggaa tgcctattcc gacaaaagga gtttaaaaag atatgccagt ctatgcgatg   35280
cgtcgatatg gctacgggaa agtgtcaaac gtataaacaa gtgaagttat gagaaatta   35340
gatttatcaa tgattccgat tgacctaaag gtaggcgagg aaatggaggt attaaccccc   35400
aaaggtgata aggttacagt aagggtggtt gaggacaaaa gagaaaatat gtgtgattgt   35460
tgcttctttg gggaaatggg tttagacctt tgtaatcacg tcaaatgcaa tttaccggag   35520
cgtgaaacaa aagatagtgt aagtttccaa gaagtaaaaa gggagagaat gcgtagtaac   35580
gagaaaggag aattattatg aaagaagtga tagacttaa aatcggtgat gaatacaagg   35640
agggtgatat actaaaggcg agagagggga tatttgtct cgtaaagaaa acgactaaca   35700
agaattacgt tgaatgttgc acttcgtgtt ggttccaaaa tacacccttg gacgtatgta   35760
```

```
tgcaaatgaa ctgtaacgca ggaaattttt attttagacc gtttgaaaca tacaaagaag   35820
gtgaggaata caacgtaggt gatctactga aaatacctaa accgggagag ccggaaagt    35880
tcatcctttc aatagtagta gaggatgata ttgtagacga atttaataat agcagttgcg   35940
gacgatgtac attcaaagac tgggtatatc ctacggatga ttgttgttca agaaacagat   36000
gtgtagattg tcttagagat ataaacttag acgatgtata ttacaaacca ttagcggagg   36060
tatcagaatg aagcaaaaga aagtgagaga ttttgaggtg ttcaaagtag tacatccgat   36120
cacagcaaac gaagtagcaa ttcaagcaat accacgggat actatttcat gcaacggatg   36180
tgccttccga aagggagatt tagaaggaat gtgcaaggtg tacgcatgtg tgaacaatca   36240
aacgttaggc tgtttagtgt tcaagaaagt aaagtagaaa ttcaaacgaa atgttacgag   36300
gttttaaaag ttaaagtatt aatttaaatg tgttgactta tgaacaaaga agttgtttta   36360
atgctctctg agctaagatt acaaattgat gatacaatta ggcgtgttgg gaaagaaagt   36420
gcctcagatg aaaagaaat tatgtctacg ttggaaggtt gtgatttgat tgatgtagac    36480
ggttgtttaa tctttcctca cgccttttta gagtggtgtg ctgactgcgg attttggaa    36540
aaggaagatg aagaaattac catctgtggg catacatgcg ctacgtataa atacgtttca   36600
aaaaacgatt taattagctt ggataaaaac ggtaatgtgt ccgttcaccc ttcattgttg   36660
tatgtctatt taaacagtgg aaaggatgtg taataataca aaggactggg aggaataccg   36720
caaagatgtg agtagctccg aaaatgtggg cgaatatatt gcagatatga tagatcacaa   36780
tgaaagagag aaactaaaaa tgcttttaga tatttgcgag aaaagcaagg atagcagcta   36840
cgatctgcct atcgactgca aaatatacct tcctttaggc tctttgttgt ttgagcatga   36900
aatgcttgat tttataacgt gggctgataa tatggggtat attcggtgtg aagaagataa   36960
gattgtaatt gtttcgtcta tgattaaaag acggcttatc gttggctctc ttaaagttat   37020
gccggagatt gtggaggcgt tcgttttgta cagaaagcat ataggttagg agtcttttag   37080
actccttttc ttatttataa acatttttgtt tttatccgtc ttcggagagt tcgagactaa   37140
tgttttaata atcaatatct ttgcaaaatt gcttttattt catactttg tacaaactaa    37200
tatttgaatt atggagattt ataattattt tcttcttgc gtgctacttg tttcgtttgt    37260
agcggcattt tgtgttaact ttgcccgaaa gacgggtata attgaacgga tgtcagtgtt   37320
tggtgattct tggttatcta aggtgttccg atggtatgat gatagatcac tgattaacga   37380
gctaatcaac tgtgatttct gcctgtcgtt ttgggcgtgt gtaatttgtt cggtgattgt   37440
gtcgatcgga acgctaaacc ctatttcat ccttacaccg atctttgcaa cacctatttg    37500
tagaattta atttaatgat tatggaaatt agaaattatg tatcaattat tccgccctc    37560
gagatcgtga gggcggttaa gtttaacggt gatgttcacg aattatcgca aatattgcca   37620
agttttgaac tactttccgc aatggatggc gtaatgatgg cacgaataaa cggcagcgct   37680
tttcgggtgt ttgataacga ttttatcgtt cttggagaaa aaattgctta ctcagttgac   37740
gaagaaacgt ttgccatatt atacgagcag gcagataagg aggtgacaga tgaacacgat   37800
taaggtaggg aatcacacgg taacggtata cgaaggcatt gatgaaatgc ctatcgtccg   37860
ttatcagaag tttaaccgtc ttatgctgat tgagtcggga gtcggtagca ctattgatga   37920
actcgatacg catttgcaac gtgctattgt ctattgcagg acacagccgg aacatacgta   37980
taacgagcta atgaatctaa ggcagtgttt caatatggcg tcgaatggcg tacatccggg   38040
aatgatgcct tttgccgcct tcgttaaatc ggtcgatgc gtggaatatc cggttaatgc    38100
gtccgactct gatctaaagg cgatatttga cagtctcagc gatgcaacta ttaacgaact   38160
ttctgaaccg tttcagaagg tcaaaaaaaa aatagaggcg gaagtatcgg tatacttccc   38220
acggatggcg gacgatcctc tgattaaaga gtattacgat attaaactat cgatgataaa   38280
agcaaagtta gacaaacttg tgaacaacgt agataacagt gggcggtga aggaaataga   38340
ggataagtta ctaaccttct tcccgcctcg aatattctac ggtactgatt cggtcgagat   38400
aaagacggac aaggagtttc aagaaatgtg cttagttatc acgcagaata tgcacataaa   38460
tgcacgtgaa atgtcggtgt ctgagtttta caccgctttc gaaatgatta agagacaggc   38520
aaaaaggagt aagaacaaat aaatttaaat caaatgcga acgaagtaaa gggaataaag   38580
tatagcgatc ttatcagcc ggacagcagt ataaaggacg ctattacgca gttggaagga    38640
ctgcaaaaga tatatgacgc tatgttaaag cgtatcgagg aaggcgcaaa aggtctgcaa   38700
aagcctattt cagaaggtgg aggcgcaacg gaggaagggc gcaaaagat agacgcctac    38760
gaaaaacaag tgcgatcatt ggcgaacgct gagatacaat tgaaattgac acttacagag   38820
acagcgcagg aaatcgcagt cttaaagaaa cagacagccg atcaaaacta tctgaataaa   38880
ctgcaagcta agttagctaa tagtatggcc ggaagctata acgctttgtc ggcacaatac   38940
gagctaaaca aaataaagat gaacaatctt tcgcaggctt atttggagaa tacggaggcg   39000
gggaagaagc ttgttaaaga gactgcggag atttacgcag cgatggataa gtatcaaaag   39060
agcacgggaa agcacacgtt aagcgtaggt aactacaaac aggcgttcga tggtttgggc   39120
ttctctgtgt cacaggtggc acgtgaactt ccttctttgg cgatcagcgc aaacacgttc   39180
ttccttgcta tttctaataa catcccgatg gttatagacg aaatacgaa gctgcgtgca    39240
gcgaacgagg cggcagcgaa ggcagggaa gcacaggtaa gtataaccgg gaaactggtt    39300
aaatctctgt tctcgtttaa taccgtgatg gtgttgatat tgaccgcctt ttctatttgg   39360
ggtaaggata taatcaactg gataggtagc ctattcaaag gtaaaacaac agtagatcag   39420
ttgaagcgat ctactaccga cttgaaagac gctatgttag aggctggaaa gagtgccgta   39480
aacgagtctg tgagactgaa catcttgtat aaagcggcta ccgattccac gcgcagccaa   39540
aacgacgtt tgtaaagctgt taaggagcta aagaaaagt atccggatca ccttaaaaac   39600
ctatcagatg aagctattat gacgggaaac gcatcaaagg aatacaagga acttgcaaaa   39660
cacattctat cggtcgcaat ggcacgtgcc tacgaggaaa agatacaaaa gaacgcaaag   39720
gaagttattg acctcgaaga aaaaagaac caagtattag aggaaggtcg gaagacttac    39780
caaaagcaac aaaaggagat cgaagaactt aaacgttcgt ctaaaggtct cggtgtcggt   39840
ggtgtggctt tggaggccggc tttacaaggg caggcgtccg catggaatac cgccaaaaag   39900
gaggcaaaga gctatgacga acaaatagca gttatcaata agtcaagtga ggaacttgct   39960
aaaaaggtgg ttattcccga tcttcttgca ggggacaaaa taggtaagac gaaggaaagg   40020
acaaagaagg actttgacct acaagctgag tatgaaaata gccgtatagc tcttattatt   40080
gattcccgtt tgaaagagca ggaagaacgt aaaaaggcaa cggctgacga actgaaaaag   40140
ctaaaggaga gcaacggga aaacaaaga gctacgcagt tatatgctga taccgtatac    40200
aatatcgagg caaaattgcg tagagacttg gagaaactgc aaaacgactg gcgggtagag   40260
gacttgcaaa tcacgcatga ccgattgagt gaacgcctaa agctgttag acgtggcacg    40320
gctgacgaac tattaattca agtgcagcta ctcgaaaacg aaagagcgca ggacgaattg   40380
cgcattaagc agtcaaccga tagcgaacag gtaaagaatg aacgtttgct tatcctgcaa   40440
agatcgtatc agcttgcatc tatccaactg caaaaggact tcactgacaa tcaagataaa   40500
```

```
cgtattattg atcggtctgt gttccgcctt aatcagcaac agcaggcgga aagtgcagcc  40560
tttaatatcg tgcagcgttc ggagaaagaa cagagccgtt tccggttaaa gttggagcgt  40620
gaaaagtggg agcaaatatt agagttaaca aggcagtacg gagagcaaat cacgggatac  40680
aacgtaaaga cggtagagga taccattaag ggaatagaca atgcaattaa gcgtgatact  40740
tccggatggg atagcaatca aggcgtgttt ggcaatctgt ttgatctcgt tttcggagac  40800
gcatttagcg ctaaagatgg taagtcgggc gcagagcgtg cagaacagtt taaagactcc  40860
atattagagg cttcggattt cgccatagaa aacctaaaga gtgttgcgca ggcaagggta  40920
gaggcggcag aggtggcagt ccaagcagcc gaaaaggaag tgtcagcccg acaaaaggtt  40980
ttggacgctg agatacaagc gagggcgaac ggatacgaca acaacgtagc aaccgcacaa  41040
aaagagcttg attttgcacg caaacaacag gaaaaagcgc ttagggataa gaagaaggcg  41100
cagaagcagc aagaacgcat agatacactt atgcaggcaa gttctttggt aaccgcaacc  41160
gctaacctat ggaaagattt aggtttggca gcgatcccgg ctattgcgtt gatgtgggga  41220
tcatttgctt ttgctaagat aaaagcctca cagctatcta aagcctcgca ggacacagag  41280
gaatacgggg acggtacggt agaaatgatt gattacgacg gttcgcacgc atccggaaac  41340
gatgtagatt taggtacgac taaggacggt aagcgtagac gggtagaacg tggtgaaatac  41400
ttcgcagtag tgaacaaacg ttcatctcag aagtataaga aactcgttcc ggacttgatt  41460
aattcgctaa ataaggggtac ttttgaacag aaatacttaa acgcctattc cggtagtgat  41520
gaagtaacga ataatgca aggttcaacg gttgatctgt ctaaggtcga aaaagatctg  41580
aaatcaatca aagagcaggg acgtgttaag tacatcacag gtgcggacgg tacgataatt  41640
gaagtaaggg gaaatattaa acgaataatt aaatcataat gaacgttaaa gatttgcggt  41700
ttaaattggg gggtgtagaa atacatcccc actactcaga gctaaaacgg aagtttggca  41760
aagagaatca acaggagttt ttcagagagt cgatagaagg aagtttaacg ctgatcggga  41820
cggactacct tcttgttaaa aatgcaagta tcgaagatat tttgtacttg cagatagaac  41880
agaaggacaa agggcaacta tcaacgcagt atcaagttat atttgagggc tatttcagta  41940
agacagattg tgagatagac agcgataacc gtacgtgcaa agtcaagata agcccacgag  42000
atgaatacca cgtatataat aaggtattg agaacaaata cgatcttatt aagcttgac  42060
ctgctttgtc gcaaatagga gtctcaaagc gtccgattgt gcaagtttac attgcgggtc  42120
catctacaat atcgaactac cttgcaggca ctcactcga aactgaggtt ttcaacgttg  42180
taacggataa caaggagcta acggataaga atttcttgc cttcttcgct gcatacaacg  42240
aaatagaggt aaaaggctgtg ccctatcagt tctttaacgg gaagtactac ggaacgaatg  42300
gaacgtacac taaattggat ggcaattttct caataaaatg gactctaagc gaaggtttaa  42360
atattggttt ccttcacttg gaaaataaag agggaactat attgtaccga tcagataaaa  42420
tcaattggag cgataaaagt tactactaca tagacgtttc tgaaataaca ttcacaagaa  42480
tagtagatga tccgacactt cctcaaaagt ttggcggaaa cactgttctt ttgcagaagc  42540
tatttcaaag aatgttgctt aaccttccgg agttggacgg taaacctacc gggaaactat  42600
catcagagga cgtttaccct accaatagca actacatgta tgccgcacca ttaaagggga  42660
actactttta tacgtctacg aaggttcaga acgagccgac agtacggt gtaaatgatg  42720
aaggcaagta ttttaccgat aacttcgttc cggctgtggc gggtactgga aagctgtatc  42780
cggtatgccg ttcacgatgg gggaatatgt cgatttgatt cgagtttgat ttgtcctatg  42840
cgccattgga ggaaagagcg agaaaggagt atgtttttaaa ggactcgttc gccatacagg  42900
acgctattag ggcgcttatt aagcaaattg atcccacttt gacgcacgaa gctacggaag  42960
aatatagtaa gttttttgtat gctgccaata accctatttc cggtgcacct tttaaggtgt  43020
tcatcacaca gaaaagcaac atcctaaagg gtgagtatga ccgtccggca aagaaggcgg  43080
aaacaaccct cagcgatata atgaagatgt tgcgtgacac gatgaaacta tattggttta  43140
tagatggcga taagtttagg atagaacata tttcttactt cataaatggc ggaagttata  43200
ccggtagtgg aacggtcggc atagacttaa caaatcttag atatgctaaa tcgggtcagc  43260
taatgacatg gaaaactaac acggtcaagt acgataaacc cgatctgcct tcacggtttg  43320
aattttcttg gatggacgat acaacaaata cgtttgcggg tttccctatt gatgtgaaat  43380
caaactacgt gcaagaggga aagaaggaag aaataagggt gtctaacttt tcgtccgatg  43440
tagattatat gctactatca ccgggtgact tttcacagga tggttttgcg ttattggggg  43500
ctacacaggt gggcgaaaaa tggaaacttc cgttcgttac gttcaacttg gtagacaaga  43560
acaataagaa gtacaccgta aaccccccaaa acggctacat gtcgttcttg cacctcgtta  43620
aatactacat gcacgatatg ccagcctcag agatagagca gggaggcgat cagacgataa  43680
gagtgagagg aataaagcgg agtatgacgc aagatttatc tttcacatac gacaccacac  43740
caaacccgt gcaactgata acaacgata taggcaacg gaaaccgata actatgactg  43800
aggatctaac aactcgccaa ataaccgtat ctttatctta caccccctta tagtaggggg  43860
tgttttcttt taaattgcta tctttgtgcc tataatcaat ttttaatca aaatggaagt  43920
acataacaac tttagtcctt tggcgtttag aaagaaagaa tctaaagcca catacgaaaa  43980
atggtacgct ttcgggaaga attatgctat ccccgcaagc gcaaatacgc ttataccttt  44040
ccagtttacc gatgtaaatg taggagaggt tcagcccgat tctattgagg ttgtagcggt  44100
aaaccaagaa accggagagg gcattaaaac aggtgtgtat gttagtcgtg acgacatgcc  44160
cgaacatggc agcgttctgt acgtgtcacc cggtaagaac tcgtttcgtg aggctttgcc  44220
acagggtaca tatcgggcgg agttttcaat cggaacacag ttttatattt caactcctt  44280
ttgtgtttat tccaggtatcg aaacaagtag caaatatcg ttgattgat attggaacga  44340
tgaaaagatc gcatatccgg atggcttat tacaacgggt gcgaacaatg acttccgta  44400
tcagatgtat gttcctgcaa ctatctgcaa accgaaatat gagttgaag aagaactaac  44460
caaacgtgcc ggatacaagt tcttagaact gcaaacgtct acgaaggtgt acgcctttac  44520
atttgttgca cctgagttta tttgtgacgc tatgcgcatt attcgcctat ctgactatat  44580
ccgaatttcg cacgatggcg aatattcaa cgccctcaac ttcgagtttg atgttgattg  44640
gcaggaacaa ttatatttgg ctgctgttga ctgccagttt gagacggact caatcataca  44700
aaaactccct tctttcaata gacgagtaaa agcgtctttt tataatgccc tattagcgaa  44760
cattgataca cctataatgt tctctcccga taccgtaggg ctgtattaca agagtatcg  44820
ggaaacagag ccagtagtca agggtaaatt gatacgggag ttatccccta ttgacttgat  44880
agatgaaaat acaactattg ccgttgattt gggtacaggt ggcgtgagaa agtttaactt  44940
ataccgaatg ttgcaggact acatttctaa agcccatgaa gatgcaacag acttttgtt  45000
acaccttcgt ggaggcgcaa cgttcggtga gggtataact ggtgctgccg cttctatcaa  45060
cgcagtagga gatgcggagg tgcagggtct aaacgcacgt gtaaccaaag ttaaatcgct  45120
tgattcggaa gattatgtaa ctgttaataa aacagccttc accgtaaaca aacaaggtga  45180
tacggctttta aatgcgctta atgcgaggg agtttcccgc ttgcagcaag atgtgtatac  45240
```

-continued

```
cggaaatgat accggaaaga tcaccaaaga aggtcaattg cagtaccttt ctgcaattat    45300
ccaacagttc ctatcatccc ctacgttcgt ttccggcttt cttggcgagg gctttaaaat    45360
atgggtcgag aatggcaatt ggcatataga atgtgacaat ttgacagtaa gacagactat    45420
gaatatattt gagctactta tccaaaagat aaggagcgtt aacggtgcat tggtcgtgtc    45480
tcagtcgaac ggaaagatta aaagcgtgtc ggaagatgaa acgaactacg ttatcacaat    45540
ggaggaagaa ggggaaacgt tccagcctaa cgatttagtt aggtgtcaag tttggacggg    45600
aagcaaagcc aaattctatt gggtcgaggt tgcaagcgtt tccggcaact ctattactgt    45660
gaaaaagtcc gaatttacag ccggaaataa gccggaaaaa ggcgatgaag tggtacagat    45720
gggtaacacg cagaacgcac aaaggcaggc tttaatctat atcacagcgc aggaaagcgg    45780
acatccgtac atagagatat tgaacggagt taaaactaaa tcgttgtccg gtacgaatag    45840
gacacgtctt ggcgatttaa gtaacataca ggactctgcg tttccggaag gacaacagcc    45900
atccggtagc ggcttgtatt gcgataacgc ttttcttcgt ggtatattct tgctgagaaa    45960
cggcaagtca gttgaggatg aagtaaacca agcgaagcaa gatgcagcca acgcagcaac    46020
agaggcggag agagcacaac agacagcgca ggaggcgaaa gatcggctta ataaatgggc    46080
tgacgatggt tttatatctc ctactgaaaa gcccgctttg attgatgaag gaaagcgtat    46140
acaggcagag tttttgcaga taaaaaataa cgctgacaaa tacggtgtat ccgttactga    46200
atataccaag gcttatgaag attatttaaa tgaacttaga taccattcag cccaacagcc    46260
ggaagatatt gcggtgcgtc cggaacttgc aaggacgcaa acgatatact acgatcggag    46320
aaacggagcg ttgaacgcta ttgcgaacgc tgcaaagagc tacgtagatg aagctgacaa    46380
gaagctaaag gagtatttag atacggagat cacagcgata cccggtaaga tcgaacttgc    46440
tgtacggagt atgaaaacgg ctgatgttaa cttgttgaag ggttcgtatg aagaaaaagc    46500
aaataactct tatagatttg ccgcatataa ctatgataca ccagttatag acgggaagaa    46560
atacactttg actgtatgct atactattgg gagtggtaat accaataaa gtgtttattc    46620
taatgctggt atgaaccaaa taacaaatct cacaactaag ggggaaagag ttatagaaag    46680
cacaaaagta accatgaaag gatataagcc gggtgaacca ttgtctttct atcaatttcc    46740
gaacggagct ttcggctcaa aagtacattg ggctgttttg actgatggca atttaggcgt    46800
aaccagttgg ataccttctg caagtgagaa gaacgtagga cttaagaact tatgttcgtt    46860
taagcgtatt actgatgcgg gatttaccta tgcttcacga tatgatgatg acggtgtaat    46920
tcttatgtta ccatcggtat tgcacaagga gtcatttgta                          46960
```

COMPOSITIONS AND METHODS FOR INHIBITING THE PROLIFERATION OF ENTEROTOXIGENIC BACTEROIDES FRAGILIS

This application is a Continuation Application of U.S. Ser. No. 17/227,286, filed on Apr. 10, 2021, which is incorporated by reference for all purposes as if fully set forth herein. A Sequence Listing XML file named "20001_0060C1.xml" created on Oct. 31, 2023, and having a size of 49,264 bytes, is filed concurrently with the specification. The sequence listing contained in the XML file is part of the specification and is herein incorporated by reference in its entirety.

BACKGROUND OF THE INVENTION

Field of the Invention

The present invention relates to compositions and methods for inhibiting the proliferation of enterotoxigenic *Bacteroides fragilis*, more specifically, a composition containing a Siphoviridae bacteriophage and a method of using the same.

Discussion of the Related Art

*Bacteroides* species comprise nearly half of the fecal flora community and are host symbionts critical to host nutrition and mucosal and systemic immunity. Among *Bacteroides* species, *Bacteroides fragilis* (*B. fragilis*) strains are opportunistic pathogens. Enterotoxigenic *B. fragilis* (ETBF) can produce a proteolytic enterotoxin, named as *B. fragilis* enterotoxin (BFT), or fragilysin, that causes secretory diarrhea and colonic epithelial damage. ETBF emerged over the past 35 years as a global etiology of diarrheal disease in animals and humans that is accompanied by colitis (Clin. Microbiol. Rev. 22: 349-369, 2009). An association of ETBF with chronic intestinal disease has been established for more than 20 years and ETBF is also positively associated with ulcerative colitis and colonic neoplasia (Gut Pathog. 9: 53-59, 2017; BMC Canc. 19: 879-882, 2019).

In addition, ETBF may cause cancer such as colorectal cancer (CRC). CRC is one of the most common cancers, accounting for approximately 10% of all cancer cases and approximately 8% of all cancer deaths. BFT is known to bind to colonic epithelial cells (CECs) and to stimulate cleavage of the tumor suppressor protein, E-cadherin. E-cadherin cleavage increases intestinal barrier permeability and augments cell signaling via the β-catenin/Wnt pathway which is constitutively activated in essentially all CRC. As a result, BFT stimulates proliferation and migration of human colon cancer cells in vitro (Gastroenterology 124: 392-400, 2003). The ability of BFT to further activate the nuclear factor-kappaB (NF-κB) pathway inducing pro-inflammatory cytokine secretion by CECs and data indicating that specific pools of NF-κB foster the initiation and promotion of epithelial tumorigenesis led to the hypothesis that ETBF were pro-inflammatory, oncogenic colonic bacteria. This hypothesis was supported by a recent small study in Turkey suggesting that ETBF colonization is more frequent in CRC patients than in controls without CRC (Clin. Microbiol. Infect. 12: 782-786, 2006).

Generally, antibiotics are used for the treatment of infectious diseases of ETBF. Here, the effectiveness of antibiotics has been continuously decreasing due to the increase of antibiotic-resistant ETBF, and the development of effective methods other than currently prescribed antibiotics is required.

Recently, the use of bacteriophages as a countermeasure against bacterial infectious diseases has attracted considerable attention. Bacteriophages are very small microorganisms infecting bacteria, and are usually simply called "phages." Once a bacteriophage infects a bacterial cell, the bacteriophage is proliferated inside the bacterial cell. After proliferation, the progeny of the bacteriophage destroys the bacterial cell wall and escapes from the host bacteria, suggesting that the bacteriophage has the ability to kill bacteria. The manner in which the bacteriophage infects bacteria is characterized by the very high specificity thereof, and thus the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria, but does not affect commensal bacteria in animals including human being. Conventional antibiotics, which have been widely used for bacterial treatment, incidentally influence many kinds of bacteria. This causes problems such as the disturbance of normal microflora. On the other hand, the use of bacteriophages does not disturb normal microflora, because the target bacterium is selectively killed. Hence, the bacteriophage may be utilized safely, which thus greatly lessens the probability of adverse actions in use compared to any other antibiotics.

Owing to the unique ability of bacteriophages to kill bacteria, bacteriophages have attracted attention as a potentially effective countermeasure against bacterial infections since their discovery, and there has been a lot of research related thereto.

Bacteriophages tend to be highly specific for bacteria. It has been shown that the attack of bacteriophage is specific, meaning that one species of bacteriophage targets only a single species of bacteria (or even a specific strain of one species). In addition, the antibacterial strength of bacteriophages may depend on the type of target bacterial strain. Therefore, it is necessary to collect many kinds of bacteriophages that are useful in order to get effective control of specific bacteria. Hence, in order to develop the effective bacteriophage utilization method in response to ETBF, many kinds of bacteriophages that exhibit antibacterial action against ETBF must be acquired. Furthermore, the resulting bacteriophages need to be screened as to whether or not they are superior to others from the aspect of antibacterial strength and spectrum.

SUMMARY OF THE INVENTION

Accordingly, the present invention has been made keeping in mind the problems encountered in the related art and is intended to solve such problems.

In one embodiment, a composition for preventing or treating an infection or disease caused by ETBF includes: a Siphoviridae bacteriophage having an ability to lyse the ETBF cells, and a pharmaceutically acceptable carrier.

In another embodiment, the Siphoviridae bacteriophage has a genome including a sequence as set forth in SEQ ID NO: 1; or a genome that has (1) a sequence having at least 90% query cover with at least 96% identity to SEQ ID NO: 1, (2) a circular genome topology, and (3) 67 open reading frames.

In another embodiment, the Siphoviridae bacteriophage has a concentration of $1\times10^1$ pfu/ml to $1\times10^{30}$ pfu/ml or $1\times10^1$ pfu/g to $1\times10^{30}$ pfu/g.

In another embodiment, the Siphoviridae bacteriophage has a concentration of $1\times10^4$ pfu/ml to $1\times10^{15}$ pfu/ml or $1\times10^4$ pfu/g to $1\times10^{15}$ pfu/g.

In another embodiment, the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, or mineral oil.

In another embodiment, the composition further includes one or more selected from the group consisting of a lubricant, a wetting agent, a sweetener, a flavor, an emulsifier, a suspending agent, and a preservative.

In another embodiment, the infection or disease caused by ETBF is acute and chronic intestinal disease, bacteremia, diarrhea, colitis, colonic neoplasia, or cancer. The cancer is colorectal cancer or colon cancer, but is not limited thereto.

In another embodiment, the composition is a solution, suspension, emulsion in oil, water-soluble medium, extract, powder, granule, tablet, or capsule.

In another embodiment, the composition further includes a second bacteriophage having an ability to lyse ETBF bacterial species and the second bacteriophage has a genome that has a sequence having less than 90% query cover with at least 96% identity to SEQ ID NO: 1.

In another embodiment, the Siphoviridae bacteriophage has major structural proteins in the sizes of approximately 25 kDa, 42 kDa, 48 kDa, and 65 kDa.

In another embodiment, the Siphoviridae bacteriophage has a latent period of 10-100 minutes and a burst size of 580-800 PFU/infected cell.

In another embodiment, the latent period is 40-80 minutes and the burst size of 240-330 PFU/infected cell.

In one embodiment, a method for preventing or treating an infection or disease caused by ETBF includes administering to a subject a Siphoviridae bacteriophage; and lysing the ETBF by the Siphoviridae bacteriophage.

In another embodiment, the Siphoviridae bacteriophage includes a sequence as set forth in SEQ ID NO: 1.

In another embodiment, the Siphoviridae bacteriophage has a concentration of $1\times10^1$ pfu/ml to $1\times10^{30}$ pfu/ml or $1\times10^1$ pfu/g to $1\times10^{30}$ pfu/g.

In another embodiment, the Siphoviridae bacteriophage has a concentration of $1\times10^4$ pfu/ml to $1\times10^{15}$ pfu/ml or $1\times10^4$ pfu/g to $1\times10^{15}$ pfu/g.

It is to be understood that both the foregoing general description and the following detailed description are exemplary and explanatory and are intended to provide further explanation of the invention as claimed.

Advantageous Effects of Invention

The compositions and methods for inhibiting the proliferation of ETBF, of the present application have high specificity against ETBF, compared with conventional compositions and methods based on antibiotics. The compositions can be used for preventing or treating ETBF infections without affecting other useful commensal bacteria and have fewer side effects. In general, when antibiotics are used, commensal bacteria are also damaged, thus entailing various side effects owing to the use thereof. Meanwhile, each antibacterial property of the bacteriophages such as antibacterial strength and spectrum (host range) are different in the case of bacteriophages exhibiting antibacterial activity against the same bacterial species and bacteriophages are usually effective only on some bacterial strains within the same bacterial species. Thus, the compositions and methods of the present application provide different effects in its industrial applications.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
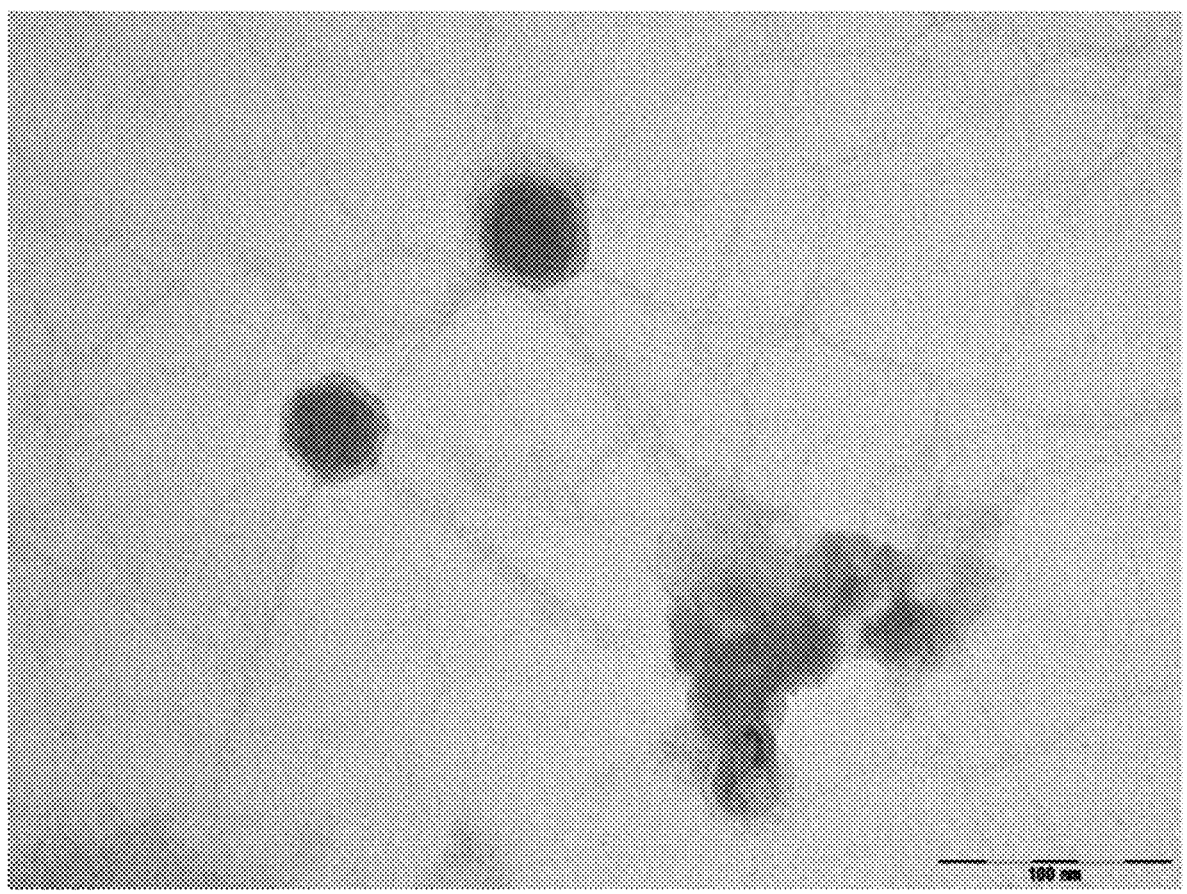
FIG. 1 is an electron micrograph showing the morphology of the bacteriophage Bac-FRP-4.

Reference will now be made in detail to embodiments of the present invention, example of which is illustrated in the accompanying drawings.

In accordance with one aspect of the present invention, the present invention provides a Siphoviridae bacteriophage, named as Bac-FRP-4, which has the ability to specifically kill ETBF and has a genome including a sequence as set forth in SEQ ID NO: 1. In some embodiment, the Siphoviridae bacteriophage contains a genome that has all the following characteristics: 1) including a sequence having at least 90% query cover with at least 96% identity to SEQ ID NO: 1, 2) having a circular genome topology, and 3) having 67 open reading frames; a genome that has all the following characteristics: 1) including a sequence having at least 92% query cover with at least 96% identity to SEQ ID NO: 1, 2) having the circular genome topology, and 3) having 67 open reading frames; a genome that has all the following characteristics: 1) including a sequence having at least 94% query cover with at least 96% identity to SEQ ID NO: 1, 2) having the circular genome topology, and 3) having 67 open reading frames; or a genome that has all the following characteristics: 1) including a sequence having at least 96% query cover with at least 96% identity to SEQ ID NO: 1, 2) having the circular genome topology, and 3) having 67 open reading frames.

The present invention also provides a method for preventing and treating infections or diseases caused by ETBF using a composition including the same as an active ingredient.

The bacteriophage Bac-FRP-4 was isolated by the present inventors and then deposited at Korea Collection for Type Cultures, Korea Research Institute of Bioscience and Biotechnology on Dec. 9, 2020 (Accession number: KCTC 14402BP).

The molecular weight of major structural proteins of the bacteriophage Bac-FRP-4 is approximately 25 kDa, 42 kDa, 48 kDa, and 65 kDa.

The latent period and burst size of the bacteriophage Bac-FRP-4 are 10-80 minutes and 580-800 PFU/infected cell, respectively, preferably 40-70 minutes and 240-330 PFU/infected cell, respectively, but are not limited thereto.

Also, the present invention provides a composition applicable for the prevention or treatment of infections or diseases caused by ETBF, which include the bacteriophage Bac-FRP-4 as an active ingredient.

Because the bacteriophage Bac-FRP-4 included in the composition of the present invention kills ETBF effectively, it is considered effective in the prevention of ETBF infections or treatment of diseases caused by ETBF. Therefore, the composition of the present invention is capable of being utilized for the prevention and treatment of diseases caused by ETBF.

The diseases caused by ETBF in the present invention include acute and chronic intestinal disease, bacteremia, diarrhea, colitis, colonic neoplasia, or cancer, but are not limited thereto.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Bac-FRP-4 is included as an active ingredient. The bacteriophage Bac-FRP-4 is included at a concentration of $1\times10^1$ pfu/ml to $1\times10^{30}$ pfu/ml or $1\times10^1$ pfu/g to $1\times10^{30}$ pfu/g, and preferably at a concentration of $1\times10^4$ pfu/ml to $1\times10^{15}$ pfu/ml or $1\times10^4$ pfu/g to $1\times10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. Then, the formulation may be in the form of a solution, suspension, or emulsion in oil or a water-soluble medium, extract, powder, granule, tablet, or capsule. A dispersing agent or stabilizer may be additionally included.

In order to improve the effectiveness of above purpose, bacteriophages that have antibacterial activity against non-ETBF bacterial species may be further included in the composition of the present invention. In addition, other kinds of bacteriophages that have antibacterial activity against ETBF may be further included in the composition of the present invention. These bacteriophages may be additionally included so as to maximize antibacterial effects, because each antibacterial property of the bacteriophages such as antibacterial strength and spectrum (host range) are different in the case of bacteriophages exhibiting antibacterial activity against the same bacterial species.

In this description, the terms "prevention" and "prevent" indicate (i) to block ETBF infections; and (ii) to inhibit the progression of diseases caused by ETBF infections.

In this description, the terms "treatment" and "treat" indicate all actions that (i) suppress diseases caused by ETBF; and (ii) alleviate the pathological condition of the diseases caused by ETBF.

In this description, the terms "diseases caused by ETBF" and "ETBF infections" indicate acute and chronic intestinal disease, bacteremia, diarrhea, colitis, colonic neoplasia, or cancer, but are not limited thereto.

In this description, the term "Latent period" indicates the time taken by a bacteriophage particle to reproduce inside an infected host cell.

In this description, the term "Burst size" indicates the number of bacteriophages produced per infected bacterium.

In this description, the terms "isolate," "isolating," and "isolated" indicate actions which isolate bacteriophages from nature by applying diverse experimental techniques and which secure characteristics that can distinguish the target bacteriophage from others, and further include the action of proliferating the target bacteriophage using bioengineering techniques so that the target bacteriophage is industrially applicable.

In this description, the terms "query cover" and "identity" are related to BLAST (Basic Local Alignment Search Tool) which is an online search tool provided by NCBI (National Center for Biotechnology Information).

In this description, the query cover is a number that describes how much of the query sequence (i.e., the sequence of genome of bacteriophage Bac-FRP-4) is covered by the target sequence (i.e., the sequence of genome of the previously reported bacteriophage). If the target sequence in the database spans the whole query sequence, then the query cover is 100%. This tells us how long the sequences are, relative to each other.

In this description, the term "identity" or "sequence identity" was measured for "query cover," and is a number that describes how similar the query sequence (i.e., the sequence of genome of bacteriophage Bac-FRP-4) is to the target sequence (i.e., the sequence of genome of the previously reported bacteriophage). More specifically, the terms "identity" or "sequence identity" refers to the percentage of identical nucleotides in the spanned sequence part of the target sequence (i.e., the sequence of genome of the previously reported bacteriophage) or the query sequence (i.e., the sequence of genome of bacteriophage Bac-FRP-4) when the query sequence (i.e., the sequence of genome of bacteriophage Bac-FRP-4) and the target sequence (i.e., the sequence of genome of the previously reported bacteriophage) are analyzed by BLAST alignment analysis. The higher the percent identity is, the more significant the match is. From above definitions for "query cover" and "sequence identity", it will be obvious for the skilled one in the art that the differences of "query cover" and/or "sequence identity" between genomes of two similar bacteriophages make the differences of ORF (open reading frame)'s numbers arranged in the two genomes, then results in the discriminative characteristics (including the range of target strain and strength of antibacterial activity) of two similar bacteriophages.

In this description, the term "Second Bacteriophage" is any bacteriophage that has the ability to specifically kill ETBF and has a genome that has a sequence having less than 90% query cover with at least 96% identity to SEQ ID NO: 1 and has different characteristics from bacteriophage Bac-FRP-4 in terms of the genome topology and the number of ORFs, wherein the genome topology of the Second Bacteriophage is linear form.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing ETBF

Samples were collected from environmental or clinical samples to isolate the bacteriophage capable of killing ETBF. Here, the ETBF strains used for the bacteriophage isolation had been previously isolated and identified as ETBF by the present inventors.

The procedure for isolating the bacteriophage is described in detail hereinafter. The collected sample was added to a BHIB (Brain Heart Infusion Broth) culture medium (calf brain infusion from 200 g, 7.7 g/L; beef heart infusion from 250 g, 9.8 g/L; proteose peptone, 10 g/L; dextrose, 2 g/L; sodium chloride, 5 g/L; disodium phosphate, 2.5 g/L) inoculated with ETBF at a ratio of 1/100, followed by stationary culture at 37 C for two days under anaerobic condition. Upon completion of the culture, centrifugation was performed at 8,000 rpm for 20 minutes and a supernatant was recovered. The recovered supernatant was inoculated with ETBF at a ratio of 1/100, followed by stationary culture at 37 C for two days under anaerobic condition. When the sample contained the bacteriophage, the above procedure was repeated a total of 5 times in order to sufficiently increase the number (titer) of the bacteriophage. After repeating the procedure 5 times, the culture solution was subjected to centrifugation at 8,000 rpm for 20 minutes. After the centrifugation, the recovered supernatant was filtered using a 0.45 m filter. The obtained filtrate was used in a typical spot assay for examining whether or not a bacteriophage capable of killing ETBF was included therein.

The spot assay was performed as follows: BHIB culture medium was inoculated with ETBF at a ratio of 1/100, followed by stationary culture at 37° C. for two days under anaerobic condition. 2 ml ($OD_{600}$ of 1.5) of the culture solution of ETBF prepared above was spread on BHIA (calf brain infusion from 200 g, 7.7 g/L; beef heart infusion from 250 g, 9.8 g/L; proteose peptone, 10 g/L; dextrose, 2 g/L; sodium chloride, 5 g/L; disodium phosphate, 2.5 g/L; agar, 15 g/L) plate. The plate was left on a clean bench for about 30 minutes to dry the spread solution. After drying, 10 l of the prepared filtrate was spotted onto the plate culture medium on which ETBF was spread and then left to dry for about 30 minutes. After drying, the plate culture medium that was subjected to spotting was incubated at 37 C for two days under anaerobic condition, and then examined for the formation of clear zones at the positions where the filtrate was dropped. In the case of the filtrate generated a clear zone, it is judged that the bacteriophage capable of killing ETBF is included therein. Through the above examination, the filtrate containing the bacteriophage having the ability to kill ETBF could be obtained.

The pure bacteriophage was isolated from the filtrate confirmed above to have the bacteriophage capable of killing ETBF. A conventional plaque assay was used to isolate the pure bacteriophage. In detail, a plaque formed in the course of the plaque assay was recovered using a sterilized tip, which was then added to the culture solution of ETBF, followed by culturing at 37 C two days under anaerobic condition. After the culturing, centrifugation was performed at 8,000 rpm for 20 minutes to obtain a supernatant. The ETBF culture solution was added to the obtained supernatant at a volume ratio of 1/50, followed by culturing at 37 C for 2 days under anaerobic condition. In order to increase the number of bacteriophages, the above procedure was repeated at least 5 times. Then, centrifugation was performed at 8,000 rpm for 20 minutes in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, a solution containing the pure bacteriophage was obtained. The procedure for isolating the pure bacteriophage was generally repeated until the generated plaques became similar to each other in size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage isolated above was confirmed to belong to the Siphoviridae bacteriophage.

The solution containing the pure bacteriophage confirmed above was subjected to the following purification process. The ETBF culture solution was added to the solution containing the pure bacteriophage at a volume ratio of 1/50 based on the total volume of the bacteriophage solution, followed by further culturing for two days under anaerobic condition. After the culturing, centrifugation was performed at 8,000 rpm for 20 minutes to obtain a supernatant. This procedure was repeated a total of 5 times in order to obtain a solution containing sufficient numbers of the bacteriophage. The supernatant obtained from the final centrifugation was filtered using a 0.45 m filter, followed by a conventional polyethylene glycol (PEG) precipitation process. Specifically, PEG and NaCl were added to 100 ml of the filtrate until reaching 10% PEG 8000/0.5 M NaCl, and then left at 4 C for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% gelatin, pH 8.0). The resulting material was referred to as a bacteriophage suspension or bacteriophage solution.

As a result, the pure bacteriophage purified above was collected, was named the bacteriophage Bac-FRP-4, and then deposited at Korea Collection for Type Culture, Korea Research Institute of Bioscience and Biotechnology on Dec. 9, 2020 (Accession number: KCTC 14402BP).

Example 2: Separation and Sequence Analysis of Genome of Bacteriophage Bac-FRP-4

The genome of the bacteriophage Bac-FRP-4 was separated as follows. The genome was separated from the bacteriophage suspension obtained using the same method as in Example 1. First, in order to remove DNA and RNA of ETBF included in the suspension, 200 U of each of DNase I and RNase A was added to 10 ml of the bacteriophage suspension and then left at 37 C for 30 minutes. After being left for 30 minutes, in order to stop the DNase I and RNase A activity, 500 l of 0.5 M ethylenediaminetetraacetic acid (EDTA) was added thereto and then left for 10 minutes. In addition, the resulting mixture was further left at 65 C for 10 minutes, and 100 l of proteinase K (20 mg/ml) was then added thereto so as to break the outer wall of the bacteriophage, followed by reaction at 37 C for 20 minutes. After that, 500 l of 10% sodium dodecyl sulfate (SDS) was added thereto, followed by reaction at 65 C for 1 hour. After reaction for 1 hour, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes in order to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 l of water. This procedure was repeated to obtain a sufficient amount of the genome of the bacteriophage Bac-FRP-4.

Information on the sequence of the genome of the bacteriophage Bac-FRP-4 obtained above was secured by performing next-generation sequencing analysis using Illumina Mi-Seq equipment from the National Instrumentation Center for Environmental Management, Seoul National University. The finally analyzed genome of the bacteriophage Bac-FRP-4 had a size of 46,960 bp, and the sequence of whole genome was expressed by SEQ ID NO: 1.

The homology (similarity) of the bacteriophage Bac-FRP-4 genomic sequence obtained above with previously reported bacteriophage genomic sequences was investigated using BLAST investigation, the genomic sequence of the bacteriophage Bac-FRP-4 was found to have a relatively high homology with the sequence of the *Bacteroides* bacteriophage B124-14 (Genbank Accession No. HE608841.1) (query cover: 86%, sequence identity: 97.16%). In addition, the number of open reading frames (ORFs) on the bacteriophage Bac-FRP-4 genome is 67, whereas *Bacteroides* bacteriophage B-124-14 has 68 open reading frames.

Based upon this result, it is concluded that the bacteriophage Bac-FRP-4 must be a novel bacteriophage different from conventionally reported bacteriophages. Further, since the antibacterial strength and spectrum of bacteriophages typically depend on the type of bacteriophage, it is considered that the bacteriophage Bac-FRP-4 can provide antibacterial activity different from that of any other bacteriophages reported previously.

Example 3: Analysis of the Major Structural Proteins of Bacteriophage Bac-FRP-4

Figure 2:
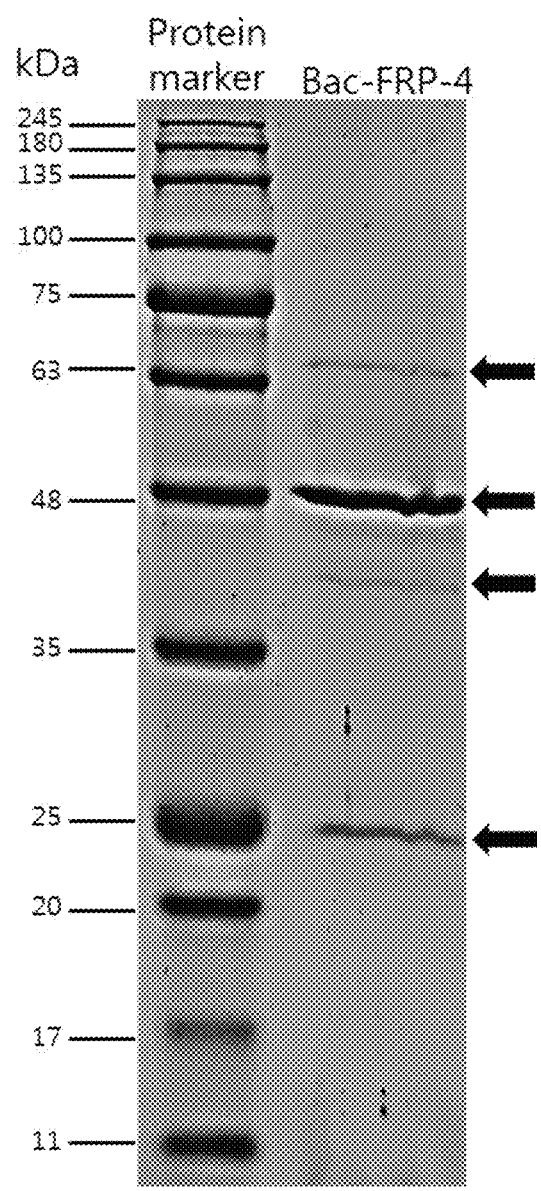
FIG. 2 is a result of the analysis for major structural proteins of bacteriophage Bac-FRP-4.

One-dimensional electrophoresis was performed to analyze the major structural proteins of the bacteriophage Bac-FRP-4. To obtain the proteins constituting the outer wall of the bacteriophage Bac-FRP-4, 200 μl of the bacteriophage suspension prepared in Example 1 was mixed with 800 μl of acetone, which was vortexed vigorously. The mixture stood at −20 C for 10 minutes. Centrifugation was performed at 13,000 rpm at 4 C for 20 minutes to eliminate supernatant, followed by air drying. The precipitate was resuspended in 50 μl of electrophoresis sample buffer (5×), which was then boiled for 5 minutes. The prepared sample was analyzed by one-dimensional electrophoresis. As a result, as shown in FIG. 2, the major structural proteins in the sizes of approximately 25 kDa, 42 kDa, 48 kDa, and 65 kDa were confirmed.

Example 4: Investigation of Ability of Bacteriophage Bac-FRP-4 to Kill ETBF

Figure 3:
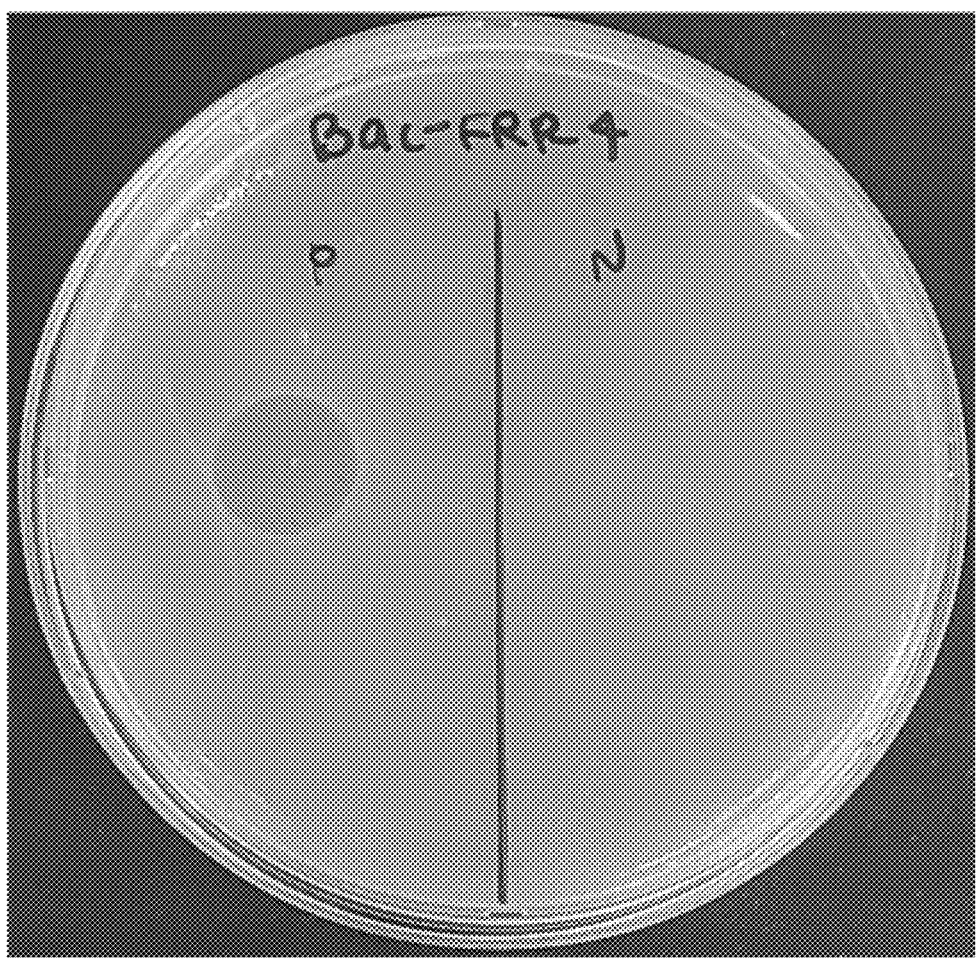
FIG. 3 is a photograph showing the results of an experiment on the ability of the bacteriophage Bac-FRP-4 to kill ETBF. The clear zone is a plaque formed by lysis of the target bacteria.

The ability of bacteriophage Bac-FRP-4 to kill ETBF was investigated. In order to investigate the killing ability, the formation of clear zones was observed using the spot assay in the same manner as described in Example 1. A total of 5 strains that had been identified as ETBF strains were used as ETBF for the investigation of killing ability. The bacteriophage Bac-FRP-4 had the ability to lyse and kill a total of 3 strains among 5 strains of ETBF as the experimental target. The experimental result thereof is presented in Table 1 and the representative result is shown in FIG. 3.

TABLE 1

Test of antibacterial activity of bacteriophage Bac-FRP-4

| Tested ETBF strain | Test result |
|---|---|
| *Bacteroides fragilis* CCARM 18105 | + |
| *Bacteroides fragilis* CCARM 18106 | − |
| *Bacteroides fragilis* CCARM 18107 | − |
| *Bacteroides fragilis* CCARM 18109 | + |
| *Bacteroides fragilis* CCARM 18110 | + |

\* +: clear lytic activity, −: no lytic activity;
CCARM: Culture Collection of Antimicrobial Resistant Microbes (Seoul, Korea)

Meanwhile, the ability of the bacteriophage Bac-FRP-4 to kill *Bordetella bronchiseptica*, *Enterococcus faecalis*, *Enterococcus faecium*, *Staphylococcus aureus*, *Streptococcus pneumonia*, *E. coli* and *Pseudomonas aeruginosa* was also investigated in a separate experiment. As a result, the bacteriophage Bac-FRP-4 did not have the ability to kill these bacteria.

Therefore, it is confirmed that the bacteriophage Bac-FRP-4 has strong ability to kill ETBF and a broad antibacterial spectrum against ETBF, suggesting that the bacteriophage Bac-FRP-4 can be used as an active ingredient of the composition for preventing and treating ETBF infections.

Example 5: Growth Characteristic of Bacteriophage Bac-FRP-4

Figure 4:
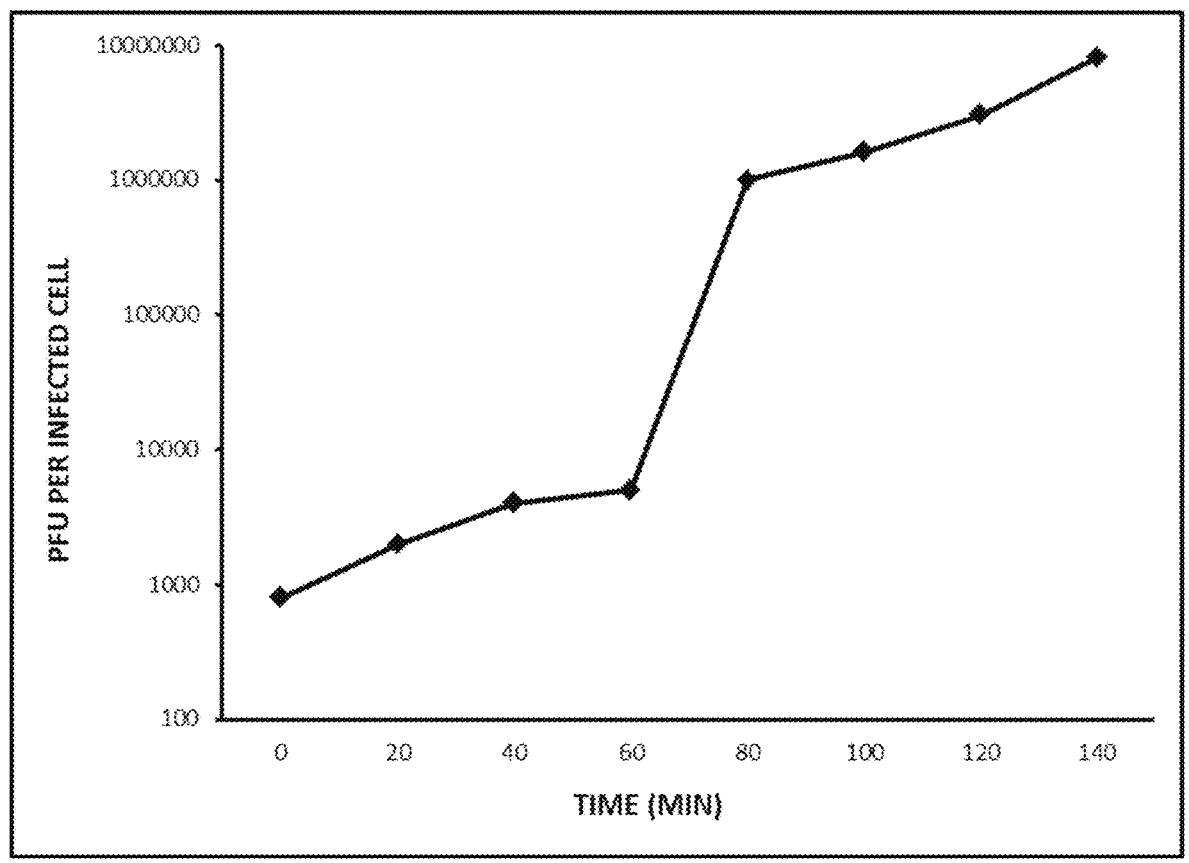
FIG. 4 is the one-step growth curve of bacteriophage Bac-FRP-4.

The growth characteristics of bacteriophage Bac-FRP-4 was analyzed by one-step growth curve analysis. One-step growth curve analysis of bacteriophage Bac-FRP-4 was performed as follows: 50 ml of BHIB (Brain heart infusion broth, Difco) culture medium was inoculated with ETBF at a ratio of 1/100 and followed by stationary culture until exponential phase ($OD_{600}$=0.4-0.5) under anaerobic condition. Upon completion of the culture, centrifugation was performed at 8,000 rpm for 5 min and a bacterial cell pellet was recovered. The recovered pellet was suspended in 50 ml of BHIB. The resulting material may be referred to as a bacterial suspension. The bacteriophage Bac-FRP-4 was mixed with the bacterial suspension at a multiplicity of infection (MOI) of 0.1 and incubated at room temperature for 10 min, and then centrifuged at 12,000 rpm for 30 seconds. After supernatants were removed, the pellets containing bacteriophage-infected bacterial cells were suspended in 50 ml of BHIB and incubated at 37 C without shaking. Aliquots were taken at 20 min intervals for 140 min, and the titers in the aliquots were immediately determined by the conventional plaque assay (FIG. 4).

The latent period of bacteriophage Bac-FRP-4 was estimated to be approximately 60±10 min with average burst size of about 320±50 pfu/infected cell.

Example 6: Experimental Example Regarding Prevention of ETBF Infection Using Bacteriophage Bac-FRP-4

100 l of a bacteriophage Bac-FRP-4 suspension ($1 \times 10^8$ pfu/ml) was added to a tube containing 9 ml of a BHIB culture medium. To another tube containing 9 ml of a BHIB culture medium, only the same amount of BHIB culture medium was further added. A culture solution of ETBF strain (CCARM 18105) was then added to each tube so that absorbance reached about 0.5 at 600 nm. After ETBF was added, the tubes were transferred to an incubator at 37 C, followed by stationary culture, during which the growth of ETBF was observed. As presented in Table 2, it was observed that the growth of ETBF was inhibited in the tube to which the bacteriophage Bac-FRP-4 suspension was added, while the growth of ETBF was not inhibited in the tube to which the bacteriophage suspension was not added.

TABLE 2

Test for bacterial growth inhibition of bacteriophage Bac-FRP-4

| Classification | $OD_{600}$ | | |
|---|---|---|---|
| | 0 minutes after initiation of cultivation | 120 minutes after initiation of cultivation | 240 minutes after initiation of cultivation |
| Bacteriophage suspension was not added | 0.5 | 0.6 | 0.7 |
| Bacteriophage suspension was added | 0.5 | 0.4 | 0.3 |

The above results indicate that the bacteriophage Bac-FRP-4 of the present invention not only inhibits the growth of ETBF but also has the ability to kill ETBF. Therefore, it is concluded that the bacteriophage Bac-FRP-4 can be used as an active ingredient of the composition for preventing the ETBF infections.

Example 7: Preventive Effect of Bacteriophage Bac-FRP-4 on the Infections of ETBF in Animal Model Preventive effect of the bacteriophage Bac-FRP-4 on weaning pigs affected by ETBF was investigated. 4 weaning pigs at 25 days of age were grouped together; total 2 groups of pigs were raised in each pig pen (1.1 m×1.0 m). Heating system was furnished and the surrounding environment was controlled. The temperature and the humidity of the pig pen were controlled consistently and the floor was cleaned every day. From the 1$^{st}$ day of the experiment, pigs of the experimental group (adding the bacteriophage) were fed with feeds adding the bacteriophage Bac-FRP-4 at $1 \times 10^8$ pfu/g according to the conventional feed supply procedure, while pigs of the control group (without adding the bacteriophage) were fed with the same feed without adding the bacteriophage Bac-FRP-4 according to the conventional procedure. From the 7$^{th}$ day of the experiment, the feeds of both groups were contaminated with $1 \times 10^8$ cfu/g of ETBF for 2 days and thereafter provided twice a day respectively for the experimental and the control groups so as to bring about the infections of ETBF. The administered ETBF suspension was prepared as follows: ETBF strain (CCARM 18109) was anaerobically cultured at 37 C for two days using a BHIB culture medium, after which the bacteria were isolated and adjusted to $10^9$ CFU/ml using physiological saline (pH 7.2). From the next day after providing contaminated feeds for 2 days (the 9$^{th}$ day of the experiment), pigs of the experimental group (adding the bacteriophage) were fed again with the feeds adding the bacteriophage Bac-FRP-4 at $1 \times 10^8$ pfu/g without contaminating ETBF according to the conventional feed supply procedure as before, while pigs of the control group (without adding the bacteriophage) were fed with the same feed without adding the bacteriophage according to the conventional procedure. From the 9$^{th}$ day of the experiment, diarrhea was examined in all test animals on a daily basis. The extent of diarrhea was determined by measuring according to a diarrhea index. The diarrhea index was measured using a commonly used Fecal Consistency (FC) score (normal: 0, soft stool: 1, loose diarrhea: 2, severe diarrhea: 3). The results are shown in Table 3.

TABLE 3

| | Fecal Consistency score | | | | | |
|---|---|---|---|---|---|---|
| | D 9 | D 10 | D 11 | D 12 | D 13 | D 14 |
| Control group (bacteriophage suspension was not administered) | 2.5 | 2.25 | 2.0 | 1.75 | 1.75 | 1.5 |
| Experimental group (bacteriophage suspension was administered) | 1.0 | 0.75 | 0.5 | 0.25 | 0 | 0 |

From the above results, it is confirmed that the bacteriophage Bac-FRP-4 of the present invention could be very effective to suppress the infections of ETBF.

Example 8: Example of Treatment of Infectious Diseases of ETBF Using Bacteriophage Bac-FRP-4

The therapeutic effect of the bacteriophage Bac-FRP-4 on diseases caused by ETBF was evaluated as follows: 40 of 8-week-old mice were divided into a total of 2 groups of 20 mice per group, after which subgroups of 5 mice each were separately reared in individual experimental mouse cages, and the experiment was performed for 7 days. On the second day of the experiment, 0.1 ml of an ETBF suspension was administered to all mice through intraperitoneal injection. The administered ETBF suspension was prepared as follows: ETBF strain (CCARM 18109) was anaerobically cultured at 37 C for two days using a BHIB culture medium, after which the bacteria were isolated and adjusted to $10^9$ CFU/ml using physiological saline (pH 7.2). At 2 hr after administration of ETBF, $10^9$ pfu of bacteriophage Bac-FRP-4 was administered through intraperitoneal injection to mice in the experimental group (administered with the bacteriophage suspension). 0.1 ml of saline was administered through intraperitoneal injection to mice in the control group (not administered with the bacteriophage suspension). Both the control and experimental groups were equally fed with feed and drinking water. Whether or not the mice survived was observed daily starting from the administration of ETBF until the end of the test. The results are shown in Table 4 below.

TABLE 4

| | Survival rate | | | | | |
|---|---|---|---|---|---|---|
| | Survival rate (%) | | | | | |
| | D 2 | D 3 | D 4 | D 5 | D 6 | D 7 |
| Control group (not administered with bacteriophage suspension) | 100 | 80 | 55 | 25 | 20 | 15 |
| Experimental group (administered with bacteriophage suspension through intraperitoneal injection) | 100 | 90 | 85 | 85 | 80 | 75 |

As is apparent from the above results, it can be concluded that the bacteriophage Bac-FRP-4 of the present invention is very effective in the treatment of diseases caused by ETBF.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Accession Number

Name of Depositary Authority: Korean Collection for Type Cultures (KCTC), Korea Research Institute of Bioscience and Biotechnology, 181 Ipsin-gil. Jeongeup-si, Jeollabuk-do 56212, Republic of Korea Accession number: KCTC 14402BP Accession date: Dec. 9, 2020

What is claimed is:

1. A method for preventing or treating an infection or disease caused by enterotoxigenic *Bacteroides fragilis* comprising:
   administering to a subject a composition containing Siphoviridae bacteriophage Bac-FRP-4 and a pharmaceutically acceptable carrier,
   wherein the Siphoviridae bacteriophage Bac-FRP-4 is deposited in the Korean Collection for Type Culture (KCTC) under accession number KCTC 14402BP and has an ability to lyse the enterotoxigenic *Bacteroides fragilis* cells and the genome sequence as set forth in SEQ ID NO: 1,
   wherein the Siphoviridae bacteriophage Bac-FRP-4 has a latent period of 10-100 minutes and a burst size of 580-800 plaque-forming units (PFU)/infected cell,
   wherein the Siphoviridae bacteriophage Bac-FRP-4 has structural proteins in the size of approximately 25 kDa, 42 kDa, 48 kDa, and 65 kDa; and
   wherein the composition has a concentration of Siphoviridae bacteriophage Bac-FRP-4 of $1\times10^4$ pfu/ml to $1\times10^{15}$ pfu/ml or $1\times10^4$ pfu/g to $1\times10^{15}$ pfu/g.

2. The method of claim 1, wherein the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, methylcellulose, methylhydroxybenzoate, propylhydroxybenzoate, talc, magnesium stearate, or mineral oil.

3. The method of claim 1, wherein the composition further contains one or more selected from the group consisting of a lubricant, a wetting agent, a sweetener, a flavor, an emulsifier, a suspending agent, and a preservative.

4. The method of claim 1, wherein the infection or disease is acute or chronic intestinal disease, selected from the group consisting of diarrhea, colitis and colonic neoplasia, bacteremia, and colorectal cancer.

5. The method of claim 1, wherein the composition is a solution, suspension, emulsion in oil, water-soluble medium, extract, powder, granule, tablet, or capsule.

* * * * *